United States Patent [19]

Lee et al.

[11] Patent Number: 4,789,395

[45] Date of Patent: Dec. 6, 1988

[54] 5-SULFUR SUBSTITUTED PYRIDINE MONOCARBOXYLIC HERBICIDES

[75] Inventors: Len F. Lee, St. Charles; Kerry L. Spear, St. Louis, both of Mo.; Mark G. Dolson, San Pablo, Calif.

[73] Assignee: Monsanto Company, St. Louis, Mo.

[21] Appl. No.: 862,340

[22] Filed: May 12, 1986

[51] Int. Cl.$^4$ .................. A01N 43/40; C07D 213/55
[52] U.S. Cl. ........................................ 71/94; 546/293;
546/292; 546/294; 546/296; 546/298
[58] Field of Search ............... 546/293, 294, 292, 296, 546/298; 71/94

[56] References Cited

PUBLICATIONS

Hackh's Chemical Dictionary, 4th Edition, McGraw-Hill Book Co., pp. 57, 82.

Primary Examiner—Jane T. Fan
Attorney, Agent, or Firm—James C. Bolding

[57] ABSTRACT

Disclosed herein are compounds of the general formula

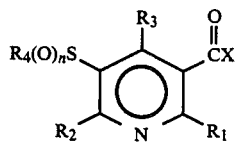

which are useful as herbicides.

24 Claims, No Drawings

5-SULFUR SUBSTITUTED PYRIDINE MONOCARBOXYLIC HERBICIDES

This invention relates to a new class of 2,6-substituted pyridinecarboxylic acid derivatives having a wide range of activity as herbicides.

Pyridine derivatives have, for many years, been investigated for use in the biological sciences. For example, 2,6-bis-(trifluoromethyl)-4-pyridinols have been found useful as herbicides and fungicides as disclosed in U.S. Pat. No. 3,748,334. Such compounds are characterized by substitution in the 4-position by a hydroxyl radical. In addition to the hydroxyl radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO Pat. No. 44,262 there are disclosed 2,6-dialkyl-3-phenylcarbamyl-5-pyridinecarboxylates and -5-cyano-compounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxyl radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intraveneous injection of such compounds.

Pyridine dicarboxylate compounds useful as herbicides are described in European Patent publication No. 133,612. These compounds have fluorinated methyl groups at the 2- and 6-positions and carboxylic acid derivative at the 3- and 5-positions.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

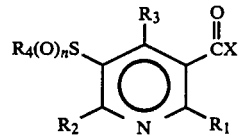

wherein:
n is from 0 to 2 inclusive; X is selected from the group consisting of a halogen, hydroxy, lower alkoxy, lower alkenoxy, lower alkynoxy, haloalkoxy, haloalkenoxy, and alkylthio;
$R_1$ and $R_2$ are independently selected from fluorinated methyl, and chlorofluorinated methyl, provided that one of $R_1$ and $R_2$ must be fluorinated methyl;
$R_4$ is selected from lower alkyl, hydrogen, cycloalkyl, aryl, and substituted aryl, aralkyl, cyano, amino, and alkylamino;
$R_3$ is selected from hydroxy, alkoxy, alkylthio, alkylsulfonyl, lower alkyl, cycloalkyl, cycloalkylalkyl;
provided that when n is 0 or 2, $R_4$ is not aryl, and further provided that when $R_3$ is methyl and $R_4$ is methyl, ethyl, or t-butyl, n is not 1 or 2.

The term "alkyl" means herein both straight and branched chain radicals which include, but are not limited to, ethyl, methyl, n-propyl, 1-ethylpropyl, 1-methylpropyl, n-butyl, 1,1-dimethylethyl, 2,2-dimethylpropyl, pentyl, isobutyl, isopropyl. The term "cycloalky" is intended to mean saturated cyclic radicals such as cyclopropyl, cyclobutyl, cyclopentyl, cyclohexyl, and cycloheptyl.

The term "lower alkyl" herein means an alkyl radical having 1 to 7 carbon atoms. The terms "lower alkenyl" and "lower alkynyl" herein mean alkenyl and alkynyl groups having 3 to 7 carbon atoms. Examples of such alkenyl groups include 2-propenyl, 2-butenyl, 3-butenyl, 2-methyl-2-propenyl, and the like. Examples of such lower alkynyl groups include 2-propynyl, and so forth.

The term "cycloalkylalkyl" is intended to mean alkyl radicals substituted with a $C_{3-6}$ cycloalkyl radical. The term "haloalkyl" is intended to mean alkyl radicals substituted with one or more halogen atoms.

The term alkenoxy and alkynoxy are intended to mean alkoxy radical substituted with an alkenyl or alkynyl group.

The term "cation" means any cation derived from a base providing a salt. Typical cations include, but are not limited to, alkali metals such as sodium, potassium, and lithium and alkaline earth metals such as calcium, organic amines, and ammonium salts, sulfonium, phosphonium salts, and other salt complexes.

The term "fluorinated methyl" means herein methyl radicals having one or more fluorine atoms attached thereto including radicals wherein all hydrogen atoms are replaced by fluorine.

The term "chlorofluorinated methyl" means herein a methyl radical having at least one hydrogen replaced by fluorine and at least one other hydrogen replaced by chlorine.

DETAILED DESCRIPTION OF THE INVENTION

The scheme shown below schematically depicts a method whereby the pyridine monocarboxylate compounds of this invention may be prepared from compounds which are known in the art. Starting with a pyridinedicarboxylate compound such as those described in European Patent Publication No. 133,612, the dicarboxylic acid chloride is prepared by treating with a chlorinating agent such as PCl₅ or SOCl₂. The 5-amino-monocarboxylate is then prepared from the 5-chlorocarbonyl compound by treatment with NaN₃ followed by a Curtius rearrangement and hydrolysis of the resulting 5-isocyanto compound. The 5-amino compound so produced is then transformed into a 5-bromo substituted pyridinemonocarboxylate, which in turn is converted to the 5-thio substituted monocarboxylate. The 5-thio compound may then be oxidized to the 5-sulfinyl or 5-sulfonyl pyridinemonocarboxylate by treatment with 1 or 2 equivalents respectively of m-chloroperbenzoic acid, respectively. These steps are shown schematically in Route 1 below, and the Examples following provide greater detail about the respective steps.

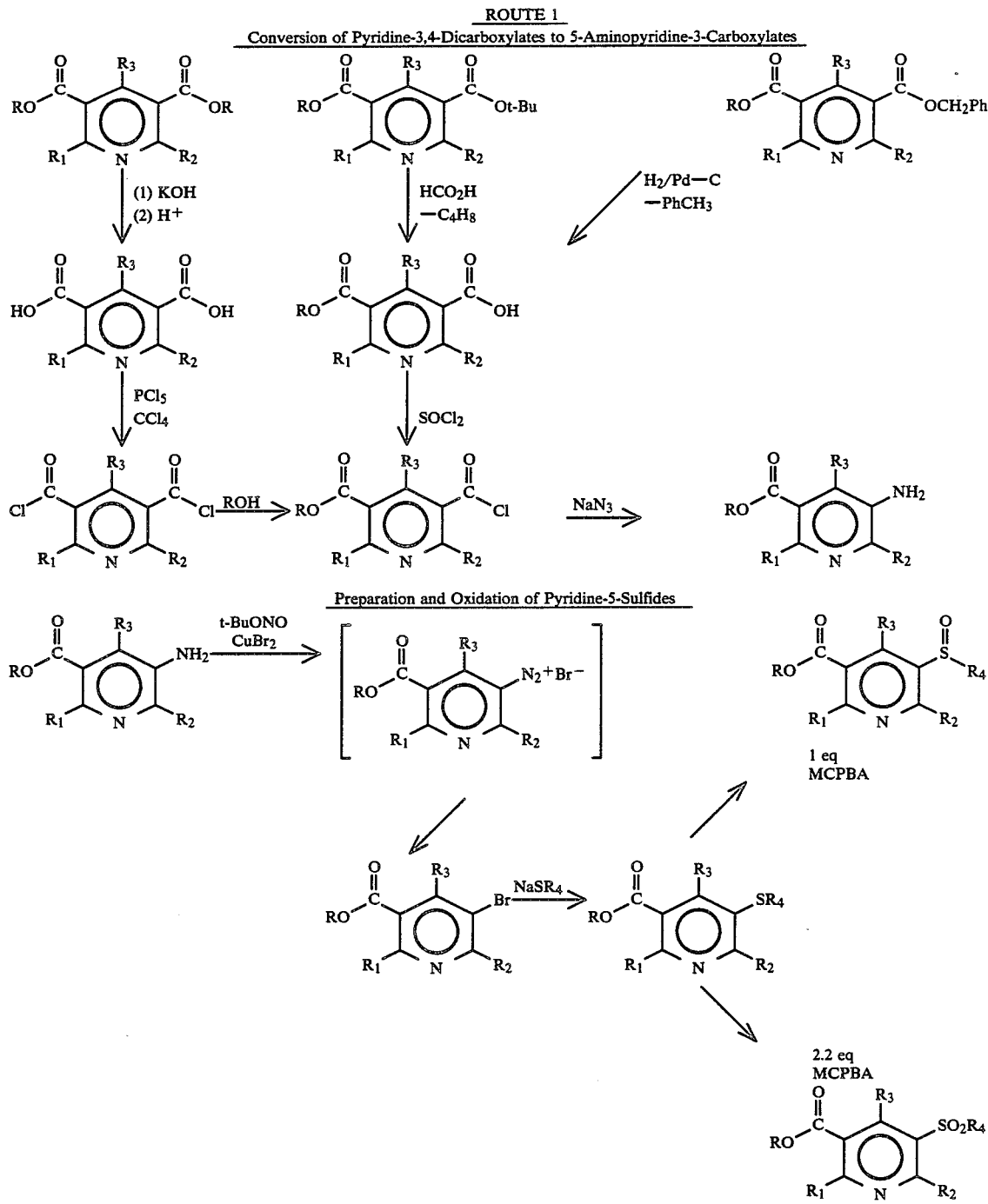

ROUTE 1
Conversion of Pyridine-3,4-Dicarboxylates to 5-Aminopyridine-3-Carboxylates Preparation and Oxidation of Pyridine-5-Sulfides Preparation of further compounds of this invention will become clear by reference to the scheme in conjunction with the following examples.

As used throughout the specification, including the Examples, the following abbreviations have the following meanings:

LDA—lithium diisopropylamide

THF—tetrahydrofuran
DME—dimethyl ether
DBU—1,8 diazobicyclo-[5.4.0]-undec-5-ene
DMF—N,N-dimethylformamide
ETFAA—ethyl trifluoroacetoacetate
MCBA—m-chlorobenzoic acid
MCPBA—m-chloroperbenzoic acid
HPLC—high pressure liquid chromatography
TLC—thin layer chromatography
n-BuLi—n-Butyl lithium
DMSO—dimethyl sulfoxide
Pd/C—hydrogenation catalyst which is palladium deposited on finely-divided carbon
TsCl—tosyl chloride.

As used in the following Examples, the terms "routine workup", "normal workup" and like terms refer to the following general techniques: the reaction mixture was diluted with 1-3 volumes of water (or 1N aq hydrochloric acid as noted) and was extracted three times with an equal volume of organic solvent. The combined organic layers were washed with one volume of water. After washing the combined aqueous phases with organic solvent (one volume), the combined organic extracts were dried over magnesium sulfate (or sodium sulfate as noted), filtered and evaporated (aspirator) to give crude product.

EXAMPLES

Preparation of 5-Bromo Pyridinemonocarboxylate precursors. Preparation of the 5-bromo substituted precursors of the compounds of the present invention from compounds known in the art is illustrated by the following Examples A-C.

EXAMPLE A

Step 1: 3-Pyridinecarboxylic acid, 5-amino-6-(difluoromethyl)-4-methyl-2-(trifluoromethyl)-, ethyl ester. To a slurry of 50 g of sodium azide, 90 mL of water and 315 mL of acetone was added 0.474 mol of product of Example 44 of European Patent Application No. 133,612 published (Feb. 27, 1985, in 35 mL of acetone with rapid stirring. An exothermic reaction resulted with vigorous gas evolution. After the reaction mixture cooled to room temperature, it was diluted with 200 mL of water and extracted with chloroform. Normal workup afforded 86.3 g (82%) of product as a white solid. Recrystallization from ethyl acetate/cyclohexane afforded analytically pure material, mp 71°-72° C.

| Elemental Analysis: | C | H | N |
|---|---|---|---|
| Calculated | 44.30 | 3.72 | 9.39 |
| Found | 44.30 | 3.73 | 9.40 |

Step 2: 3-Pyridinecarboxylic acid, 5-bromo-6-(difluoromethyl)-4-methyl-2-(trifluoromethyl)-, ethyl ester. To a solution of 6.25 g (0.028 mol) of cupric bromide, 3.61 g (0.035 mol) of t-butyl nitrite and 80 mL of acetonitrile was added a solution of 7.0 g (0.023 mol) of product of Step 1 above in 7 mL of acetonitrile. This was stirred at room temperature for 1.5 hours, then poured into 200 mL of 10% hydrochloric acid and extracted with chloroform (3×50 mL). Normal workup gave a yellow oil which was filtered through a short silica gel column (2% ethyl acetate/cyclohexane) to give 7.54 g (91%) of product as a colorless liquid; $n_D^{25}$ 1.470.

| Elemental Analysis: | C | H | N | Br |
|---|---|---|---|---|
| Calculated | 36.49 | 2.51 | 3.87 | 22.07 |
| Found | 36.47 | 2.53 | 3.86 | 21.99 |

EXAMPLE B

Step 1: 3-Pyridinecarboxylic acid, 5-amino-6-(difluoromethyl)-4-ethyl-2-(trifluoromethyl)-, ethyl ester. A mixture of 35.0 g (0.103 mol) of product of Example 46 of European Patent Application No. 133,612 published Feb. 27, 1985, and 60 mL of thionyl chloride was refluxed overnight. The excess thionyl chloride was removed in vacuo and the acid chloride was diluted with 10 mL of acetone, and added to a slurry of 14.3 g of NaN₃, 25 ml of H₂O, and 90 ml of acetone. An exothermic reaction occurred with vigorous gas evolution. After the reaction mixture cooled to room temperature, 300 mL of water was added and the product was extracted into chloroform. Normal workup gave 30.9 g (96%) of product as a tan solid. Recrystallization from ethyl acetate/cyclohexane afforded analytically pure material, mp 92°-94° C.

| Elemental Analysis: | C | H | N |
|---|---|---|---|
| Calculated | 46.16 | 4.20 | 8.97 |
| Found | 46.08 | 4.23 | 8.94 |

Step 2: 3-Pyridinecarboxylic acid, 5-bromo-6-(difluoromethyl)-4-ethyl-2-(trifluoromethyl)-, ethyl ester. To a solution of 5.09 g (0.023 mol) of cupric bromide, 2.94 g (0.029 mol) of t-butyl nitrite and 70 mL of anhydrous acetonitrile was added a solution of 6.0 g (0.019 mol) of product of Step 1 in 5 mL acetonitrile. This was stirred at room temperature for 2 hours, then poured into 10% hydrochloric acid (200 mL) and extracted with chloroform (3×40 mL). Normal workup afforded 6.95 g of light yellow oil. Kugelrohr distillation (125° C. @ 1.0 torr) gave 6.35 g (89%) of product as a white solid. Recrystallization from cyclohexane gave analytically pure material, mp 39°-41° C.

| Elemental Analysis: | C | H | N | Br |
|---|---|---|---|---|
| Calculated | 38.32 | 2.95 | 3.72 | 21.25 |
| Found | 38.47 | 2.99 | 3.77 | 21.40 |

EXAMPLE C

Step 1: 3-Pyridinecarboxylic acid, 5-amino-6-(difluoromethyl)-4-isobutyl-2-(trifluoromethyl)-, ethyl ester. The product of Example 16 (6.0 g, 15.1 mmol) of European Patent Application No. 133,612 published Feb. 27, 1985, was added to 0.95 g of 89% potassium hydroxide (15.1 mmol) and 35 mL of ethanol and was stirred at room temperature for 1 day. The reaction mixture was poured into 135 mL of water, washed with ether (2×20 mL) and acidified with concentrated hydrochloric acid. The product was extracted into ether (2×50 mL), which was worked up as usual to afford 4.91 g (88%) of the desired mono-acid as an off-white solid suitable for further transformation. This was refluxed overnight with thionyl chloride (25 mL). The excess thionyl chloride was removed in vacuo and the resulting acid chloride was added dropwise to a rapidly-stirred slurry of 1.8 g of sodium azide in 15 mL of 4:1 acetone:water. This was stirred at room temperature for the weekend, then diluted with 75 mL of water and extracted with ether (3×20 mL). Workup as usual afforded 4.66 g (91% overall) of product as a tan solid. Recrystallization from cyclohexane gave analytically pure material, mp 68°–70° C.

| Elemental Analysis: | C | H | N |
|---|---|---|---|
| Calculated | 49.91 | 5.04 | 8.23 |
| Found | 49.23 | 4.97 | 8.26 |

Step 2: 3-Pyridine carboxylic acid, 5-bromo-6-(difluoromethyl)-4-isobutyl-2-(trifluoromethyl)-, ethyl ester. To a refluxing solution of 3.15 g (14.1 mmol) of cupric bromide, 1.81 g (17.6 mmol) of t-butyl nitrite and 40 mL of acetonitrile, was slowly added a solution of 4.0 g (11.8 mmol) of product of Step 1 in 2.5 mL of acetonitrile. After 30 minutes the reaction mixture was cooled to room temperature and added to 200 mL of 20% hydrochloric acid. The product was extracted into ether (2×150 mL). Workup as usual afforded 4.56 g of yellow oil. Purification by HPLC of this material using 2% ethyl acetate/cyclohexane afforded 2.89 g (60%) of product in the first fraction as a light yellow oil.

Anal. Cal'd. for $C_{14}H_{15}BrF_5NO_2$: C, 41.60; H, 3.74; Br, 19.77; N, 3.47. Found: C, 41.70; H, 3.79; Br, 19.67; N, 3.46.

PREPARATION OF COMPOUNDS OF THE INVENTION

Preparation of the 5-sulfur substituted compounds of the present invention in which the sulfur substituent has various valence states, starting with the 5-bromo compounds of Examples A–C, is shown in detail in the following Examples 1–41.

Unless otherwise noted, the sodium salt of the thiol used was prepared in situ by the addition of the thiol (1.1 eq) to a suspension of sodium hydride (1.1 eq) in tetrahydrofuran (THF; 1.6–1.8 L/mol of substrate). The sodium hydride, a dispersion in oil, was first freed from the oil by washing with THF (2×). A solution of the appropriate bromopyridine (1.0 eq) in THF (1.6–1.8 L/mol) was added dropwise to a suspension of the appropriate sodium thiolate (1.1 eq) in THF (1.6–1.8 L/mol of substrate). After stirring at room temperature (2–24 hours), routine acid/methylene chloride workup afforded the crude product.

EXAMPLE 1

6-(Difluoromethyl)-4-methyl-5-methylthio-2-(trifluoromethyl)-3-pyridinecarboxylic acid, ethyl ester. Prepared from product of Example A (17.0 g, 46.9 mmol) and sodium methanethiolate (Fluka; 3.61 g, 51.6 mmol) as described above. Kugelrohr distillation (115° C. at 0.22 torr) afforded the product as a pale yellow oil (15.08 g).

| Elemental Analysis: | C | H | N |
|---|---|---|---|
| Calculated | 43.77 | 3.67 | 4.25 |
| Found | 43.88 | 3.66 | 4.24 |

EXAMPLE 2

6-(Difluoromethyl)-4-ethyl-5-methylthio-2-(trifluoromethyl)-3-pyridinecarboxylic acid, ethyl ester. Prepared from product of Example B (17.0 g, 45.2 mmol) and sodium methanethiolate (Fluka; 3.5 g, 49.7 mmol) as described above. Kugelrohr distillation (115° C. at 0.36 torr) afforded the product as a pale yellow oil (15.42 g).

| Elemental Analysis: | C | H | N |
|---|---|---|---|
| Calculated | 45.48 | 4.11 | 4.08 |
| Found | 45.57 | 4.09 | 4.14 |

EXAMPLE 3

6-(Difluoromethyl)-4-(2-methylpropyl)-5-methylthio-2-(trifluoromethyl)-3-pyridinecarboxylic acid, ethyl ester. Prepared from product of Example C (17.0 g, 42.1 mmol) and sodium methanethiolate (Fluka; 3.25 g, 46.3 mmol) as described above. Kugelrohr distillation (105° C. at 0.18 torr) afforded the product as a yellow oil (15.56 g) which solidified near room temperature.

| Elemental Analysis: | C | H | N |
|---|---|---|---|
| Calculated | 48.51 | 4.89 | 3.77 |
| Found | 48.53 | 4.92 | 3.76 |

EXAMPLE 4

6-(Difluoromethyl)-5-ethylthio-4-methyl-2-(trifluoromethyl)-3-pyridinecarboxylic acid, ethyl ester. Prepared from product of Example A (21.0 g, 58 mmol), sodium hydride (3.1 g of a 50% dispersion in oil, 64 mmol) and ethanethiol (Aldrich; 4.74 mL, 64 mmol) as described above. Kugelrohr distillation (130° C. at 0.50 torr) afforded the product as a pale yellow oil.

| Elemental Analysis: | C | H | N |
|---|---|---|---|
| Calculated | 45.48 | 4.11 | 4.08 |
| Found | 45.54 | 4.13 | 4.08 |

EXAMPLE 5

6-(Difluoromethyl)-4-ethyl-5-ethylthio-2-(trifluoromethyl)-3-pyridinecarboxylic acid, ethyl ester. Prepared from product of Example B (21.0 g, 56 mmol), sodium hydride (2.95 g of a 50% dispersion in oil, 61.4 mmol) and ethanethiol (Aldrich; 4.55 mL, 61.4 mmol) as described above. Kugelrohr distillation (110° C. at 0.20 torr) afforded the product as a pale yellow oil (19.2 g).

| Elemental Analysis: | C | H | N |
|---|---|---|---|
| Calculated | 47.06 | 4.51 | 3.92 |
| Found | 46.87 | 4.51 | 3.90 |

EXAMPLE 6

6-(Difluoromethyl)-5-ethylthio-4-(2-methylpropyl)-2-(trifluoromethyl)-3-pyridinecarboxylic acid, ethyl ester. Prepared from product of Example C (21.0 g, 52 mmol), sodium hydride (2.75 g of a 50% dispersion in oil, 57 mmol) and ethanethiol (Aldrich; 4.22 mL, 57 mmol) as described above. Kugelrohr distillation (120° C. at 0.43 torr) afforded the product as a pale yellow oil (19.60 g).

| Elemental Analysis: | C | H | N |
| --- | --- | --- | --- |
| Calculated | 49.86 | 5.23 | 3.63 |
| Found | 50.03 | 5.25 | 3.62 |

EXAMPLE 7

6-(Difluoromethyl)-4-methyl-5-phenylthio-2-(trifluoromethyl)-3-pyridinecarboxylic acid, ethyl ester. Prepared from product of Example A (16.0 g, 44.2 mmol), sodium hydride (2.3 g of a 50% dispersion in oil, 48.6 mmol) and thiophenol (5.0 mL, 48.6 mmol) as described above. Kugelrohr distillation (150° C. at 0.48 torr) afforded the product as a pale yellow oil (16.27 g).

| Elemental Analysis: | C | H | N |
| --- | --- | --- | --- |
| Calculated | 52.17 | 3.61 | 3.58 |
| Found | 52.11 | 3.64 | 3.55 |

EXAMPLE 8

6-(Difluoromethyl)-4-ethyl-5-phenylthio-2-(trifluoromethyl)-3-pyridinecarboxylic acid, ethyl ester. Prepared from product of Example B (2.6 g, 6.9 mmol), sodium hydride (0.37 g of a 50% dispersion in oil, 7.6 mmol) and thiophenol (0.78 mL, 7.6 mmol) as described above. Kugelrohr distillation (115° C. at 0.14 torr) afforded a yellow solid (2.98 g) which was recrystallized from petroleum ether to afford the product as a white solid (2.36 g).

| Elemental Analysis: | C | H | N |
| --- | --- | --- | --- |
| Calculated | 53.33 | 3.98 | 3.46 |
| Found | 53.33 | 3.99 | 3.40 |

EXAMPLE 9

6-(Difluoromethyl)-4-(2-methylpropyl)-5-phenylthio-2-trifluoromethyl)-3-pyridinecarboxylic acid, ethyl ester. Prepared from product of Example C (21.0 g, 52 mmol), sodium hydride (2.75 g of a 50% dispersion in oil, 57 mmol) and thiophenol (5.85 mL, 57 mmol) as described above. Kugelrohr distillation (150° C. at 0.47 torr) afforded the product as a pale yellow oil (22.11 g).

| Elemental Analysis: | C | H | N |
| --- | --- | --- | --- |
| Calculated | 55.42 | 4.65 | 3.23 |
| Found | 55.45 | 4.65 | 3.21 |

EXAMPLE 10

6-(Difluoromethyl)-4-methyl-5-(1-methylethylthio)-2-(trifluoromethyl)-3-pyridinecarboxylic acid, ethyl ester. Prepared from product of Example A (17.0 g, 46.9 mmol), sodium hydride (2.5 g of a 50% dispersion in oil, 52 mmmol) and 2-propanethiol (4.83 mL, 52 mmol) as described above. Kugelrohr distillation (125° C. at 0.48 torr) afforded the product as a yellow oil (16.75 g).

| Elemental Analysis: | C | H | N |
| --- | --- | --- | --- |
| Calculated | 47.06 | 4.51 | 3.92 |

| Elemental Analysis: | C | H | N |
| --- | --- | --- | --- |
| Found | 47.12 | 4.56 | 3.90 |

EXAMPLE 11

6-(Difluoromethyl)-4-ethyl-5-(1-methylethylthio)-2-(trifluoromethyl)-3-pyridinecarboxylic acid, ethyl ester. Prepared from product of Example B (17.0 g, 45.2 mmol), sodium hydride (2.4 g of a 50% dispersion in oil, 50 mmol) and 2-propanethiol (4.64 mL, 50 mmol) as described above. Kugelrohr distillation (120° C. at 0.56 torr) afforded the product as a yellow oil (16.55 g).

| Elemental Analysis: | C | H | N |
| --- | --- | --- | --- |
| Calculated | 48.51 | 4.89 | 3.77 |
| Found | 48.54 | 4.94 | 3.73 |

EXAMPLE 12

6-(Difluoromethyl)-4-(2-methylpropyl)-5-(1-methylethylthio)-2-(trifluoromethyl)-3-pyridinecarboxylic acid, ethyl ester. Prepared from product of Example C (17.0 g, 42.1 mmol), sodium hydride (2.24 g of a 50% dispersion in oil, 46.7 mmol) and 2-propanethiol (4.34 mL, 46.7 mmol) as described above. Kugelrohr distillation (125° C. at 0.77 torr) afforded the product as a yellow oil (16.59 g).

| Elemental Analysis: | C | H | N |
| --- | --- | --- | --- |
| Calculated | 51.12 | 5.55 | 3.51 |
| Found | 51.13 | 5.56 | 3.51 |

EXAMPLE 13

6-(Difluoromethyl)-4-methyl-5-[(1,1-dimethyl)ethylthio]-2-(trifluoromethyl)-3-pyridinecarboxylic acid, ethyl ester. Prepared from product of Example A (16.5 g, 45.6 mmol), sodium hydride (2.4 g of a 50% dispersion in oil, 50.1 mmol) and tert-butanethiol (5.69 mL, 50.1 mmol) as described above. Recrystallization (methanol-water) afforded the product as a yellow solid (13.65 g).

| Elemental Analysis: | C | H | N |
| --- | --- | --- | --- |
| Calculated | 48.51 | 4.89 | 3.77 |
| Found | 48.65 | 4.89 | 3.77 |

EXAMPLE 14

6-(Difluoromethyl)-4-ethyl-5-(1,1-dimethylethylthio)-2-(trifluoromethyl)-3-pyridinecarboxylic acid, ethyl ester. Prepared from product of Example B (16.5 g, 43.9 mmol), sodium hydride (2.3 g of a 50% dispersion in oil, 48.25 mmol) and tert-butanethiol (5.48 mL, 48.25 mmol) as described above. Recrystallization (methanol-water) afforded the product as a yellow solid (14.21 g).

| Elemental Analysis: | C | H | N |
| --- | --- | --- | --- |
| Calculated | 49.86 | 5.23 | 3.61 |
| Found | 50.06 | 5.24 | 3.61 |

EXAMPLE 15

6-(Difluoromethyl)-4-(2-methylpropyl)-5-(1,1-dimethylethylthio)-2-(trifluoromethyl)-3-pyridine-carboxylic acid, ethyl ester. Prepared from product of Example C (17.0 g, 42.1 mmol), sodium hydride (2.24 g of a 50% dispersion in oil, 46.7 mmol) and tert-butanethiol (5.26 mL, 46.7 mmol) as described above. Kugelrohr distillation (130° C. at 0.77 torr) followed by recrystallization (petroleum ether) afforded the product as a white solid (14.61 g).

| Elemental Analysis: | C | H | N |
|---|---|---|---|
| Calculated | 52.29 | 5.85 | 3.39 |
| Found | 52.52 | 5.89 | 3.35 |

SYNTHESIS OF PYRIDYL SULFOXIDES FROM PYRIDYL SULFIDES—GENERAL PROCEDURE

Solid m-chloroperbenzoic acid (MCPBA; 1.0 eq.) was added in one portion to a cooled (0° C.) solution of the appropriate sulfenylpyridine (1.0 eq) in methylene chloride (2.5–3.2 L/mol). After stirring at 0° C. for ½ hour, the reaction mixture was stirred at room temperature overnight. The solvent was evaporated and the residue was stirred with saturated aqueous sodium bicarbonate (5.0–7.0 L/mol. of substrate) until gas evolution ceased. After extraction with methylene chloride (3×), the combined organic layers were dried (MgSO$_4$), filtered and evaporated (aspirator) to afford the crude product.

EXAMPLE 16

6-(Difluoromethyl)-5-methylsulfinyl-4-methyl-2-(trifluoromethyl)-3-pyridinecarboxylic acid, ethyl ester. Prepared from product of Example 1 (5.75 g, 17.5 mmol) and MCPBA (3.4 g of an 85% mixture with MCBA; 17.5 mmol) as described above. Recrystallization (ether) afforded the product as a white solid (5.23 g).

| Elemental Analysis: | C | H | N |
|---|---|---|---|
| Calculated | 41.74 | 3.50 | 4.06 |
| Found | 41.76 | 3.52 | 4.03 |

EXAMPLE 17

6-(Difluoromethyl)-5-methylsulfinyl-4-ethyl-2-(trifluoromethyl)-3-pyridinecarboxylic acid, ethyl ester. Prepared from product of Example 2 (5.8 g, 16.9 mmol) and MCPBA (3.43 g, of an 85% mixture with MCBA, 16.9 mmol) as described above. Recrystallization (ether/petroleum ether) afforded the product as a white solid (5.39 g).

| Elemental Analysis: | C | H | N |
|---|---|---|---|
| Calculated | 43.45 | 3.93 | 3.90 |
| Found | 43.52 | 3.94 | 3.86 |

EXAMPLE 18

6-Difluoromethyl)-5-methylsulfinyl-4-(2-methylpropyl)-2-(trifluoromethyl)-3-pyridinecarboxylic acid, ethyl ester. Prepared from product of Example 3 (5.8 g, 15.6 mmol) and MCPBA (3.17 g of an 85% mixture with MCBA, 15.6 mmol) as described above. Recrystallization (ether) afforded the product as a white solid (4.19 g).

| Elemental Analysis: | C | H | N |
|---|---|---|---|
| Calculated | 46.51 | 4.68 | 3.62 |
| Found | 46.57 | 4.70 | 3.58 |

EXAMPLE 19

6-(Difluoromethyl)-5-ethylsulfinyl-4-methyl-2-(trifluoromethyl)-3-pyridinecarboxylic acid, ethyl ester. Prepared from product of Example 4 (7.0 g, 20.4 mmol) and MCPBA (4.15 g of an 85% mixture with MCBA, 20.4 mmol) as described above. Recrystallization (ether) afforded the product as a white solid (6.74 g).

| Elemental Analysis: | C | H | N |
|---|---|---|---|
| Calculated | 43.45 | 3.93 | 3.90 |
| Found | 43.44 | 3.94 | 3.88 |

EXAMPLE 20

6-(Difluoromethyl)-4-ethyl-5-ethylsulfinyl-2-(trifluoromethyl)-3-pyridinecarboxylic acid, ethyl ester. Prepared from product of Example 5 (7.0 g, 19.6 mmol) and MCPBA (3.98 g of an 85% mixture with MCBA, 19.6 mmol) as described above. Recrystallization (ether/petroleum ether) afforded the product as a white solid (6.56 g).

| Elemental Analysis: | C | H | N |
|---|---|---|---|
| Calculated | 45.04 | 4.32 | 3.75 |
| Found | 45.12 | 4.33 | 3.74 |

EXAMPLE 21

6-(Difluoromethyl)-5-ethylsulfinyl-4-(2-methylpropyl)-2-(trifluoromethyl)-3-pyridinecarboxylic acid, ethyl ester. Prepared from product of Example 6 (7.0 g, 18.1 mmol) and MCPBA (3.7 g of an 85% mixture with MCBA, 18.1 mmol) as described above. Recrystallization (ether/petroleum ether) afforded the product as a white solid (6.23 g).

| Elemental Analysis: | C | H | N |
|---|---|---|---|
| Calculated | 47.88 | 5.02 | 3.49 |
| Found | 47.90 | 5.04 | 3.45 |

EXAMPLE 22

6-(Difluoromethyl)-5-phenylsulfinyl-4-methyl-2-(trifluoromethyl)-3-pyridinecarboxylic acid, ethyl ester. Prepared from product of example 7 (6.0 g, 15.3 mmol) and MCPBA (3.11 g of an 85% mixture with MCBA, (ether/petroleum ether) afforded the product as a white solid (4.85 g).

| Elemental Analysis: | C | H | N |
|---|---|---|---|
| Calculated | 50.12 | 3.46 | 3.44 |
| Found | 50.28 | 3.47 | 3.43 |

EXAMPLE 23

6-(Difluoromethyl)-5-phenylsulfinyl-4-ethyl-2-(trifluoromethyl)-3-pyridinecarboxylic acid, ethyl ester. Prepared from product of Example 8 (6.1 g, 15.1 mmol) and MCPBA (2.9 g of an 85% mixture with MCBA, 15.1 mmol) as described above. Recrystallization (ether/petroleum ether) afforded the product as a white solid (4.46 g).

| Elemental Analysis: | C | H | N |
| --- | --- | --- | --- |
| Calculated | 51.31 | 3.83 | 3.32 |
| Found | 51.46 | 3.83 | 3.30 |

EXAMPLE 24

6-(Difluoromethyl)-5-phenylsulfinyl-4-(2-methylpropyl)-2-(trifluoromethyl)-3-pyridinecarboxylic acid, ethyl ester. Prepared from product of Example 9 (8.0 g, 18.5 mmol) and MCPBA (3.75 g of an 85% mixture with MCBA, 18.5 mmol) as described above. Recrystallization (ether/petroleum ether) afforded the product as a white solid (5.75 g).

| Elemental Analysis: | C | H | N |
| --- | --- | --- | --- |
| Calculated | 53.45 | 4.49 | 3.12 |
| Found | 53.26 | 4.56 | 3.09 |

EXAMPLE 25

6-(Difluoromethyl)-5-(2-propylsulfinyl)-4-methyl-2-(trifluoromethyl)-3-pyridinecarboxylic acid, ethyl ester. Prepared from product of Example 10 (6.06 g, 16.96 mmol) and MCPBA (3.44 g of an 85% mixture with MCBA, 16.96 mmol) as described above. Recrystallization (ether/petroleum ether) afforded the product as a white solid (4.65 g).

| Elemental Analysis: | C | H | N |
| --- | --- | --- | --- |
| Calculated | 45.04 | 4.32 | 3.75 |
| Found | 45.07 | 4.21 | 3.77 |

EXAMPLE 26

6-(Difluoromethyl)-5-(2-propylsulfinyl)-4-ethyl-2-(trifluoromethyl)-3-pyridinecarboxylic acid, ethyl ester. Prepared from product of Example 11 (5.89 g, 15.86 mmol) and MCPBA (3.22 g of an 85% mixture with MCBA, 15.86 mmol) as described above. Recrystallization (ether/petroleum ether) afforded the product as a white solid (6.2 g).

| Elemental Analysis: | C | H | N |
| --- | --- | --- | --- |
| Calculated | 46.51 | 4.68 | 3.62 |
| Found | 46.50 | 4.71 | 3.62 |

EXAMPLE 27

6-(Difluoromethyl)-5-(2-propylsulfinyl)-4-(2-methylpropyl)-2-(trifluoromethyl)-3-pyridinecarboxylic acid, ethyl ester. Prepared from product of Example 12 (5.97 g, 14.95 mmol) and MCPBA (3.03 g of an 85% mixture with MCBA, 14.95 mmol) as described above. Recrystallization (ether/petroleum ether) afforded the product as a white solid (4.03 g).

| Elemental Analysis: | C | H | N |
| --- | --- | --- | --- |
| Calculated | 49.15 | 5.34 | 3.37 |
| Found | 49.18 | 5.37 | 3.37 |

SYNTHESIS OF PYRIDYL SULFONES FROM PYRIDYL SULFIDES—GENERAL PROCEDURE

Solid m-chloroperbenzoic acid (MCPBA; 2.2 eq) was added in one portion to a cooled (0° C.) solution of the appropriate sulfenylpyridine (1.0 eq) in methylene chloride (3.7–3.8 L/mol). After stirring at 0° C. for ½ hour, the reaction mixture was stirred at room temperature overnight. The solvent was evaporated and the residue was stirred with sat. aq. sodium bicarbonate (7.5–11 L/mol of substrate) until gas evolution ceased. After extraction with methylene chloride (3×), the combined organic layers were dried (MgSO$_4$), filtered and evaporated (aspirator) to afford the crude product.

EXAMPLE 28

6-(Difluoromethyl)-5-methylsulfonyl-4-methyl-2-(trifluoromethyl)-3-pyridinecarboxylic acid, ethyl ester. Prepared from product of Example 1 (5.75 g, 17.5 mmol) and MCPBA (7.85 g of an 80% mixture with MCBA, 38.5 mmol) as described above. Recrystallization (methylene chloride/petroleum ether) afforded the product as a white solid (3.45 g).

| Elemental Analysis: | C | H | N |
| --- | --- | --- | --- |
| Calculated | 39.89 | 3.35 | 3.88 |
| Found | 39.86 | 3.37 | 3.87 |

EXAMPLE 29

6-(Difluoromethyl)-5-methylsulfonyl-4-ethyl-2-(trifluoromethyl)-3-pyridinecarboxylic acid, ethyl ester. Prepared from product of Example 2 (5.8 g, 16.9 mmol), and MCPBA (8.0 g of an 80% mixture with MCBA, 37.2 mmol) as described above. Recrystallization (ether) afforded the product as a white solid (5.47 g).

| Elemental Analysis: | C | H | N |
| --- | --- | --- | --- |
| Calculated | 41.60 | 3.76 | 3.73 |
| Found | 41.68 | 3.77 | 3.69 |

EXAMPLE 30

6-(Difluoromethyl)-5-methylsulfonyl-4-(2-methylpropyl)-2-(trifluoromethyl)-3-pyridinecarboxylic acid, ethyl ester. Prepared from product of Example 3 (5.8 g, 15.6 mmol) and MCPBA (7.4 g of an 80% mixture with MCBA, 34.3 mmol) as described above. Recrystallization (ether/petroleum ether) afforded the product as a white solid (4.39 g).

| Elemental Analysis: | C | H | N |
| --- | --- | --- | --- |
| Calculated | 44.66 | 4.50 | 3.47 |
| Found | 44.66 | 4.49 | 3.45 |

EXAMPLE 31

6-(Difluoromethyl)-5-ethylsulfonyl-4-methyl-2-(trifluoromethyl)-3-pyridinecarboxylic acid, ethyl ester. Prepared from product of Example 4 (7.0 g, 20.4 mmol) and MCPBA (9.7 g of an 80% mixture with MCBA, 44.9 mmol) as described above. Recrystallization (methylene chloride/petroleum ether) afforded the product as a white solid (6.15 g).

| Elemental Analysis: | C | H | N |
|---|---|---|---|
| Calculated | 41.60 | 3.76 | 3.73 |
| Found | 41.68 | 3.76 | 3.70 |

EXAMPLE 32

6-(Difluoromethyl)-5-ethylsulfonyl-4-ethyl-2-(trifluoromethyl)-3-pyridinecarboxylic acid, ethyl ester. Prepared from product of Example 5 (7.0 g, 19.6 mmol) and MCPBA (9.3 g of an 80% mixture with MCBA, 43.1 mmol) as described above. Recrystallization (ether) afforded the product as a white solid (6.59 g).

| Elemental Analysis: | C | H | N |
|---|---|---|---|
| Calculated | 43.19 | 4.14 | 3.60 |
| Found | 43.08 | 4.12 | 3.56 |

EXAMPLE 33

6-(Difluoromethyl)-5-ethylsulfonyl-4-(2-methylpropyl)-3-pyridinecarboxylic acid, ethyl ester. Prepared from product of Example 6 (7.0 g, 18.1 mmol) and MCPBA (8.23 g of an 80% mixture with MCBA, 38.1 mmol) as described above. Recrystallization (ether/petroleum ether) afforded the product as a white solid (5.88 g).

| Elemental Analysis: | C | H | N |
|---|---|---|---|
| Calculated | 46.04 | 4.83 | 3.36 |
| Found | 46.12 | 4.86 | 3.32 |

EXAMPLE 34

6-(Difluoromethyl)-5-phenylsulfonyl-4-methyl-2-(trifluoromethyl)-3-pyridinecarboxylic acid, ethyl ester. Prepared from product of Example 7 (6.0 g, 15.3 mmol) and MCPBA (7.25 g of an 80% mixture with MCBA, 33.6 mmol) as described above. Recrystallization (methylene chloride/petroleum ether) afforded the product as a white solid (4.26 g).

| Elemental Analysis: | C | H | N |
|---|---|---|---|
| Calculated | 48.23 | 3.33 | 3.31 |
| Found | 48.24 | 3.35 | 3.20 |

EXAMPLE 35

6-(Difluoromethyl)-5-phenylsulfonyl-4-ethyl-2-trifluoromethyl-3-pyridinecarboxylic acid, ethyl ester. Prepared from product of Example 8 (6.0 g, 14.8 mmol) and MCPBA (6.7 g of an 80% mixture with MCBA, 32.5 mmol) as described above. Recrystallization (ether) afforded the product as a white solid (4.57 g).

| Elemental Analysis: | C | H | N |
|---|---|---|---|
| Calculated | 49.43 | 3.69 | 3.20 |
| Found | 49.49 | 3.73 | 3.19 |

EXAMPLE 36

6-(Difluoromethyl)-5-phenylsulfonyl-4-(2-methylpropyl)-2-(trifluoromethyl)-3-pyridinecarboxylic acid, ethyl ester. Prepared from product of Example 9 (8.0 g, 18.5 mmol) and MCPBA (8.8 g of an 80% mixture with MCBA, 40.7 mmol) as described above. Recrystallization (ether) afforded the product as a white solid (5.22 g).

| Elemental Analysis: | C | H | N |
|---|---|---|---|
| Calculated | 51.61 | 4.33 | 3.01 |
| Found | 51.68 | 4.32 | 3.00 |

EXAMPLE 37

6-(Difluoromethyl)-5-(1-methylethylsulfonyl)-4-methyl-2-trifluoromethyl-3-pyridinecarboxylic acid ethyl ester. Prepared from product of Example 10 (6.7 g, 17.2 mmol) and MCPBA (7.7 g of an 80% mixture with MCBA, 37.8 mmol) as described above. Recrystallization (chloroform/petroleum ether) afforded the product as a white solid (4.18 g).

| Elemental Analysis: | C | H | N |
|---|---|---|---|
| Calculated | 43.19 | 4.14 | 3.60 |
| Found | 43.22 | 4.08 | 3.61 |

EXAMPLE 38

6-(Difluoromethyl)-5-(1-methylethylsulfonyl)-4-ethyl-2-(trifluoromethyl)-3-pyridinecarboxylic acid, ethyl ester. Prepared from product of Example 11 (5.85 g, 15.75 mmol) and MCPBA (6.0 g of an 80% mixture with MCBA, 34.65 mmol) as described above. Recrystallization (chloroform/petroleum ether) afforded the product as a white solid (2.6 g).

| Elemental Analysis: | C | H | N |
|---|---|---|---|
| Calculated | 44.66 | 4.50 | 3.47 |
| Found | 44.69 | 4.52 | 3.45 |

EXAMPLE 39

6-(Difluoromethyl)-5-(1-methylethylsulfonyl)-4-(2-methylpropyl)-2-(trifluoromethyl)-3-pyridinecarboxylic acid, ethyl ester. Prepared from product of Example 12 (5.36 g, 12.4 mmol) and MCPBA (5.55 g of an 80% mixture with MCBA, 27.3 mmol) as described above. HPLC (eluent-1:4/ethyl acetate:petroleum ether) followed by recrystallization (chloroform/petroleum ether) afforded the product as a white solid (2.56 g).

| Elemental Analysis: | C | H | N |
|---|---|---|---|
| Calculated | 47.33 | 5.14 | 3.25 |
| Found | 47.34 | 5.16 | 3.23 |

EXAMPLE 40

6-(Difluoromethyl)-5-(1,1-dimethylethylsulfonyl)-4-methyl-2-(trifluoromethyl)-3-pyridinecarboxylic acid, ethyl ester. Prepared from product of Example 13 (5.0 g, 13.46 mmol) and MCPBA (6.0 g of an 80% mixture with MCBA, 29.6 mmol) as described above. HPLC (eluent-1:4/chloroform:petroleum ether) followed by recrystallization (ethyl acetate/petroleum ether) afforded the product as a white solid (1.29 g).

| Elemental Analysis: | C | H | N |
|---|---|---|---|
| Calculated | 44.66 | 4.50 | 3.47 |
| Found | 44.78 | 4.54 | 3.46 |

EXAMPLE 41

6-(Difluoromethyl)-5-(1,1-dimethylethylsulfonyl)-4-ethyl-2-(trifluoromethyl)-3-pyridinecarboxylic acid, ethyl ester. Prepared from product of Example 14 (5.3 g, 13.75 mmol) and MCPBA (7.8 g of an 80% mixture with MCBA, 38.5 mmol) as described above. HPLC (eluent-1:1/chloroform:cyclohexane) followed by recrystallization (chloroform/petroleum ether) afforded the product as a white solid (1.51 g).

| Elemental Analysis: | C | H | N |
|---|---|---|---|
| Calculated | 46.04 | 4.82 | 3.36 |
| Found | 46.15 | 4.84 | 3.34 |

The following Examples 42–48 show an alternative method of preparation of compounds of this invention. In this method, a pyridinemonocarboxylate with hydrogen (rather than halogen) substitution at the 5-position is used as an intermediate. Examples D-E show the preparation of the pyridinemonocarboxylate precursors.

EXAMPLE D

Step 1: Methyl 2-acetyl-3-amino-4,4,4-trifluoro-2-butenoate. To a 1 liter, four-necked flask equipped with nitrogen inlet, thermometer, and mechanical stirrer was charged 499.74 g (490 ml, 3.84 mol) of methyl acetoacetate and 12.9 g (0.115 mol) of potassium t-butoxide. The resulting mixture was stirred while 391 g (4.04 mol) of trifluoroacetonitrile was added. The reaction mixture was washed with hexane and the resulting solid was dried in vacuo affording 535 g (62%) of the enamine as a yellow solid; mp 63°–65° C.

Step 2: Methyl 2,6-bis(trifluoromethyl)-4-hydroxy-3-pyridinecarboxylate. To a flame dried 3-liter, four-necked flask equipped with nitrogen inlet, low temperature thermometer, 500 ml addition funnel and mechanical stirrer is charged 147 ml (1.05 mol) of diisopropylamine and 600 ml of dry tetrahydrofuran. The resulting solution is cooled to −78° C. using an acetone-dry ice bath. To this is slowly added 618 ml (1.05 mol) of 1.7M n-BuLi in hexane at such a rate that the reaction temperature was kept below −60° C. After stirring at −78° C. for 1 hour, a solution of 106 g (0.50 mol) of methyl 2-acetyl-3-amino-4,4,4-trifluoro-2-butenoate from Step 1 in 400 ml of dry THF was added in such a rate that the reaction temperature was kept below −60° C. The reaction mixture turned yellow and a solid suspension formed. After 1 hour of stirring at −78° C., the reaction mixture was treated with 59.5 ml (0.50 mol) of ethyl trifluoroacetate in such rate that the reaction temperature was kept below −60° C. This reaction mixture was left at −78° C. for 1 hour, then warmed to room temperature (the yellow suspension disappeared and a yellow solution was formed) and stirred for 2 hours. The resulting solution was poured into 1 L of H$_2$O and extracted with ether (3×700 ml). The combined ether layers were washed with H$_2$O (2×800 ml) and the combined aqueous layers were acidified with concentrated HCl (pH ∼2). The acidified aqueous layer was extracted with CHCl$_3$ (3×1000 ml), dried (MgSO$_4$) and reduced in vacuo affording 120.85 g of a yellow solid. The crude was recrystallized from ether/hexane to give 103.28 g (71%) of pyridine product; mp 62°–75° C.

Step 3: Methyl 4-methoxy-2,6-bis(trifluoromethyl)-3-pyridinecarboxylate. A mixture of methyl iodide (32.3 ml, 0.519 mol), potassium carbonate (14.4 g, 0.104 mol), and product of Step 2 (25.0 g, 0.086, 5 mol) in acetone (100 ml) was refluxed for 18 hours and concentrated. The residue was dissolved in ether and washed with water. The ether layer was worked up as usual. The crude product, a yellow solid (27.25 g), was recrystallized (chloroform petroleum ether) to afford white rods (22.95 g), yield—88%; mp 101°–103° C.

Anal. Calc'd. for C$_{10}$H$_7$N$_1$O$_3$F$_6$: C, 39.62; H, 2.33; N, 4.62. Found: C, 39.76; H, 2.33; N, 4.62.

EXAMPLE E

Methyl 4-isopropoxy-2,6-bis(trifluoromethyl)-3-pyridinecarboxylate

This compound was obtained by reaction of 2-iodopropane (50 ml, 0.50 mol) and potassium carbonate (16.6 g, 0.12 mol) with a solution of product of Step 2 of Example D (30.0 g, 0.10 mol) and acetone (150 ml) as described above. The crude product, an orange oil (38.91 g), was purified via HPLC (4% ethyl acetate/petroleum ether) followed by recrystallization (petroleum ether) to afford the product as a white solid (27.67 g). Yield—84%; mp 51°–52° C.

Anal. Calc'd. for C$_{12}$H$_{11}$N$_1$O$_3$F$_6$: C, 43.51; H, 3.35; N, 4.23. Found: C, 43.57; H, 3.38; N, 4.22.

Sulfidation of Pyridine Anions with Phenyl Disulfide—General Procedure. A solution of pyridine product from Example D or E (1 eq) in dry THF (1.5–2.0 mL/mmol) was added to a cooled (−78° C.) solution of LDA, generated in situ by the addition of n-butyl lithium (1.5 eq) to a solution of diisopropylamine (1.5 eq) in dry THF (1.5–2.0 mL/mmol) to form a pyridine carbanion. After stirring at −78° C. for 1 hour, a solution of phenyl disulfide (1.2 eq) in dry THF (0.5 mL/mmol) was added dropwise. The stirring was continued at −78° C. for 2 hours before warming to room temperature for an additional 1 hour. Addition to 1N hydrochloric acid (3 mL/mmol base), followed by routine chloroform workup afforded the crude product.

Sulfidation of Pyridine Anions with Methyl Disulfide—General Procedure. A solution of pyridine (1 eq) in dry THF (1.8–2.0 mL/mmol) was added to a cooled (−78° C.) solution of LDA, generated in situ by the addition of n-butyl lithium (1.5 eq) to a solution of diisopropylamine (1.5 eq) in dry THF (1.1–1.3 mL/mmol) to form a pyridine carbanion as above. After stirring at −78° C. for 1 hour, methyl disulfide (1.2 eq) was added dropwise. Stirring was continued at −78° C. for 2 hours before being warmed to room temperature for an additional 1 hour. Addition to 1N hydrochloric acid (3 mL/mmol base), followed by routine chloroform workup afforded the crude product.

EXAMPLE 42

Methyl 4,5-bis(Methylthio)-2,6-bis(trifluoromethyl)-3-pyridinecarboxylate

A. Obtained by the addition of methyl disulfide (2.85 mL, 31.7 mmol) to the anion of product of Example D (8.0 g, 26.4 mmol) as described above. The crude product, a dark orange solid (12.19 g), was recrystallized (methanol) to afford the product as a fluffy white solid (6.72 g). Yield—70%; mp, 85.5°–86.5° C.

Anal. Calc'd for $C_{22}H_9NO_2S_2F_6$: C, 36.17; H, 2.48; N, 3.83. Found: C, 36.14; H, 2.50; N, 3.83.

B. Obtained by the addition of methyl disulfide (4.05 mL, 45 mmol) to the anion of product of Example E (12.6 g, 38 mmol) as described above. The crude product, an orange oil (15.48 g) was recrystallized (methanol) to afford a white solid (7.37 g) which was identical to the product described above. Yield—53%.

OXIDATION OF PYRIDYL SULFIDES—GENERAL PROCEDURE

The appropriate amount of MCPBA (1.0 eq for oxidation to sulfoxides, 2.2 eq for oxidation to sulfones) was added in one portion to a cooled (0°) solution of sulfide in methylene chloride (3–4 mL/mmol). After stirring at 0° for 1 hour, the reaction mixture was warmed to room temperature for 3–24 hours and added to saturated aq sodium bicarbonate (2–4 mL/mmol peracid). After extraction with methylene chloride (3×), the organic layers are combined, dried ($MgSO_4$) and evaporated (aspirator) to give the crude product.

EXAMPLE 43

Methyl 4,5-bis(Methylsulfonyl)-2,6-bis(trifluoromethyl)-3-pyridinecarboxylate. Obtained by the addition of MCPBA (6.5 g of an 80–90% mixture with MCBA 30.0 mmol) to a solution of product of Example 42 (2.2 g, 60 mmol) as described above. After stirring at room temperature overnight (17 hours), routine workup afforded the crude product, a yellow solid (2.36 g), which was recrystallized (chloroform) to afford the product as a white solid (2.19 g). Yield—85%; mp 202°–205° C.

Anal. Cal'd for $C_{22}H_2NO_6S_2F_6$: C, 30.77; H, 2.11, N, 3.26; S, 14.94. Found: C, 30.78; H, 2.13; N, 3.24; S, 14.90.

EXAMPLE 44

Methyl 4-Hydroxy-5-phenylthio-2,6-bis(trifluoromethyl)-3-pyridinecarboxylate. Obtained by the addition of phenyl disulfide (8.5 g, 39 mmol) to the anion of product of Example D (10.0 g, 33 mmol) as described above. The crude product, an orange oil (16.17 g), was purified via HPLC (20:80:3/ethyl acetate:petroleum ether, glacial acetic acid) followed by crystallization (methanol-water) to afford the product as fine white needles (7.92 g). Yield—60%; mp 98.5°–100.5° C.

Anal. Calc'd for $C_{15}H_9NO_3SF_6$: C, 45.35; H, 2.28; N, 3.53. Found: C, 45.48; H, 2.35; N, 3.49.

EXAMPLE 45

Methyl 4-Hydroxy-5-phenylsulfinyl-2,6-bis(trifluoromethyl)-3-pyridinecarboxylate. Solid MCPBA (4.3 g of an 80–90% mixture with MCBA, 19.9 mmol) was added in one portion to a cooled (0°) solution of product of Example 44 (3.6 g, 9.0 mmol) in methylene chloride (25 mL). After stirring at 0° C. for 1 hour, the reaction mixture was warmed to room temperature for an additional 25 hours. The usual aqueous-methylene chloride workup afforded a white solid (8.45 g) which contained considerable MCBA (as well as, presumably MCPBA). After taking this material up in ether, the insoluble product was filtered off and recrystallized (ether-chloroform) to afford a white solid (2.20 g). Yield—59%; mp—141°–142° C.

Anal. Calc'd for: $C_{15}H_9NO_4SF_6$: C, 43.59; H, 2.19; N, 3.39. Found: C, 43.67; H, 2.41; N, 3.38.

EXAMPLE 46

Methyl 4-(1-Methylethoxy)-5-phenylthio-2,6-bis(trifluoromethyl)-3-pyridinecarboxylate. Obtained by the addition of phenyl disulfide (9.8 g, 45 mmol) to the anion of product of Example E (12.6 g, 38 mmol) as described above. The crude product, a yellow oil (18.11 g), was purified via HPLC (1% ether-petroleum ether) to afford the product as a pale yellow oil (13.26 g). Yield—79%; $n_D^{25}$—1,5069.

Anal. Calc'd for: $C_{18}H_{15}NO_3SF_6$: C, 49,20; H, 3.44; N, 3.19. Found: C, 49.31; H, 3.47; N, 3.20.

EXAMPLE 47

Methyl 4-(1-Methylethoxy)-5-phenylsulfonyl-2,6-bis(trifluoromethyl)-3-carboxylate. Obtained by the addition of MCPBA (4.0 g of an 80–90% mixture with MCBA, 18.5 mmol) to a solution of product of Example 46 (3.7 g, 8.4 mmol) as described above. After stirring at room temperature for 19 hours, routine workup afforded the crude product, a yellow solid (4.74 g), which was recrystallized (petroleum ether-ether) to afford the product as white cubes (3.72 g). Yield—94%; mp 90°–92° C.

Anal. Calc'd for $C_{28}H_{15}NO_5SF_6$: C, 45.86; H, 3.21; N, 2.97. Found: C, 45.70; H, 3.25; N, 3.03.

EXAMPLE 48

Methyl 4-(1-Methylethoxy)-5-phenylsulfinyl-2,6-bis(trifluoromethyl)-3-pyridinecarboxylate. Obtained by the addition of MCPBA (1.70 g of an 80–90% mixture with MCBA, 8.35 mmol) to a solution of product of Example 46 (3.67 g, 8.35 mmol) as described above. After stirring at room temperature for 20 hours, routine workup afforded the crude product, a yellow solid (3.98 g) which was recrystallized (ether) to afford the product as a white solid (3.54 g). Yield—93%, mp 104°–105° C.

Anal. Calc'd for: $C_{17}H_{15}NO_4SF_6$: C, 47.48; H, 3.32; N, 3.08. Found: C, 47.51; H, 3.36; N, 3.02.

Using preparative techniques similar to those described in the foregoing Examples 1–41 in detail, additional compounds of this invention were prepared. These additional compounds are shown in the following Table 1, along with a physical property for each.

TABLE 1

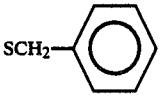

| Example | R2 | R3 | R4 | R5 | R6 | MP °C. | $n_D^{25}$ |
|---|---|---|---|---|---|---|---|
| 42 | CF3 | OCH2CH3 | CH2CH3 | SC≡N | CF2H | | |
| 43 | CF3 | OCH2CH3 | CH3 | SH | CF2H | 61.0–63.0 | |
| 44 | CF3 | OCH2CH3 | CH2CH3 | SCH2–C6H5 | CF2H | | 1.515 |
| 45 | CF3 | OCH2CH3 | CH(CH3)2 | SCH2CH3 | CF3 | | 1.475 |
| 46 | CF3 | OCH2CH3 | CH(CH3)2 | S(O)CH2CH3 | CF3 | | 1.485 |
| 47 | CF3 | OCH2CH3 | CH(CH3)2 | S(O)2CH2CH3 | CF3 | 79.0–81.0 | |
| 48 | CF3 | OCH3 | CH2CH(CH3)2 | SCH2CH3 | CF3 | | 1.4770 |
| 49 | CF2H | OCH3 | CH2CH(CH3)2 | S(O)2CH2CH3 | CF3 | 98.0–100.0 | |
| 50 | CF3 | OCH2CH3 | CH2CH3 | S(O)CH2–C6H5 | CF2H | 118.0–121.0 | |
| 51 | CF3 | OCH2CH3 | (CH2)2CH3 | SCH2CH3 | CF2H | | 1.472 |
| 52 | CF3 | OCH2CH3 | (CH2)2CH3 | S(O)CH2CH3 | CF2H | | |
| 53 | CF3 | OCH2CH3 | (CH2)2CH3 | S(O)2CH2CH3 | CF2H | 61.0–63.0 | |
| 54 | CF3 | OCH3 | CH2CH(CH3)2 | SCH2CH3 | CF2H | | 1.474 |
| 55 | CF3 | OCH3 | CH2CH(CH3)2 | S(O)2CH2CH3 | CF2H | 69.0–71.0 | |
| 56 | CF3 | OCH3 | CH2CH(CH3)2 | S(O)CH2CH3 | CF2H | 129.0 | |
| 57 | CF2H | OCH3 | CH2CH(CH3)2 | S(O)CH2CH3 | CF3 | 129.0 | |
| 58 | CF2H | OH | CH2CH(CH3)2 | SCH2CH3 | CF3 | 115.0–117.0 | |
| 59 | CF3 | SCH3 | CH2CH(CH3)2 | SCH2CH3 | CF2H | | 1.504 |
| 60 | CF2H | OCH2CH3 | CH2CH(CH3)2 | SCH2CH3 | CF3 | | 1.474 |
| 61 | CF3 | SCH3 | CH2CH(CH3)2 | S(O)CH2CH3 | CF2H | 81.0–83.0 | |
| 62 | CF2H | Cl | CH2CH(CH3)2 | SCH2CH3 | CF3 | | 1.488 |
| 63 | CF2H | SCH3 | CH2CH(CH3)2 | SCH2CH3 | CF3 | | 1.505 |

TABLE 1-continued

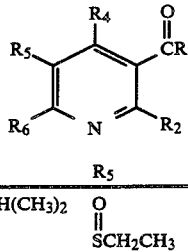

| Example | R₂ | R₃ | R₄ | R₅ | R₆ | MP °C. | $n_D^{25}$ |
|---|---|---|---|---|---|---|---|
| 64 | CF₂H | SCH₃ | CH₂CH(CH₃)₂ | $\underset{SCH_2CH_3}{\overset{O}{\|}}$ | CF₃ | 63.0–65.0 | |
| 65 | CF₂H | OH | CH₂CH(CH₃)₂ | $\overset{O}{\underset{\overset{\|}{O}}{\underset{\|}{S}CH_2CH_3}}$ | CF₃ | 188.0–190.0 | |
| 66 | CF₂H | Cl | CH₂CH(CH₃)₂ | $\overset{O}{\underset{\overset{\|}{O}}{\underset{\|}{S}CH_2CH_3}}$ | CF₃ | 66.0–62.0 | |
| 67 | CF₂H | SCH₃ | CH₂CH(CH₃)₂ | $\overset{O}{\underset{\overset{\|}{O}}{\underset{\|}{S}CH_2CH_3}}$ | CF₃ | 73.0–75.0 | |
| 68 | CF₃ | OCH₃ | CH₂CH(CH₃)₂ | SCH₃ | CF₂H | | 1.476 |
| 69 | CF₃ | OCH₃ | CH₂CH(CH₃)₂ | $\underset{SCH_3}{\overset{O}{\|}}$ | CF₂H | 108.0–110.0 | |
| 70 | CF₃ | OCH₃ | CH₂CH(CH₃)₂ | $\overset{O}{\underset{\overset{\|}{O}}{\underset{\|}{S}NH_2}}$ | CF₂H | 80.0–82.0 | |
| 71 | CF₃ | OCH₃ | CH₂CH(CH₃)₂ | $\overset{O}{\underset{\overset{\|}{O}}{\underset{\|}{S}N(CH_3)_2}}$ | CF₂H | 90.0–91.0 | |
| 72 | CF₃ | OCH₃ | CH₂CH(CH₃)₂ | $\overset{O}{\underset{\overset{\|}{O}}{\underset{\|}{S}NHCH_3}}$ | CF₂H | 130.0–132.0 | |
| 73 | CF₃ | OCH₃ |  | SCH₂CH₃ | CF₂H | 30.4–36.5 | |
| 74 | CF₃ | OCH₃ |  | $\underset{SCH_2CH_3}{\overset{O}{\|}}$ | CF₂H | 136.9–137.3 | |
| 75 | CF₃ | OCH₃ | 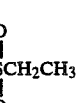 | $\overset{O}{\underset{\overset{\|}{O}}{\underset{\|}{S}CH_2CH_3}}$ | CF₂H | 114.1–115.0 | |
| 76 | CF₂H | OCH₃ |  | SCH₂CH₃ | CF₃ | 54.0–55.7 | |
| 77 | CF₂H | OCH₃ |  | $\underset{SCH_2CH_3}{\overset{O}{\|}}$ | CF₃ | 78.4–82.1 | |

TABLE 1-continued

| Example | $R_2$ | $R_3$ | $R_4$ | $R_5$ | $R_6$ | MP °C. | $n_D^{25}$ |
|---|---|---|---|---|---|---|---|
| 78 | $CF_2H$ | $OCH_3$ | ◇ | $SCH_2CH_3$ (with =O, =O) | $CF_3$ | 118.9-119.8 | |
| 79 | $CF_3$ | $OCH_3$ | $CH_2CH(CH_3)_2$ | $SN_3$ (with =O, =O) | $CF_2H$ | 82.0 | |
| 80 | $CF_3$ | $OCH_3$ | $CH(CH_3)_2$ | $SCH_2CH_3$ | $CF_2H$ | | 1.478 |

PRE-EMERGENT HERBICIDE EXAMPLES

As noted above, many of the compounds of this invention have been found to be effective as pre-emergent and post-emergent herbicides. Table 2 summarizes results of tests conducted to determine the pre-emergent herbicidal activity of the compounds of this invention on common weeds.

The pre-emergent tests are conducted as follows:

Top soil is placed in aluminum pans and compacted to a depth of 0.95 to 1.27 cm. from the top of the pan. On the top of the soil is placed a predetermined number of seeds or vegetative propagules of various plant species. The soil required to level fill the pans after seeding or adding vegatative propagules is weighed into a pan. A known amount of the active ingredient applied in acetone as a solvent is thoroughly mixed with the soil, and the herbicide/soil mixture is used as a cover layer for prepared pans. In Table 2 below the amount of active ingredient is equal to the rate of 11.2 kg/ha. After treatment, the pans are moved to a greenhouse bench where they are watered from below as needed to give adequate moisture for germination and growth.

Approximately 10-14 days (usually 11 days) after seeding and treating, the pans are observed and the results recorded. In some instances, a second observation is made approximately 24-28 days after seeding and treating, and these observations are indicated in the following tables by an asterisk (*) immediately following the Example number.

Table 2 below summarizes the results of the pre-emergent herbicidal activity tests of compounds of this invention in weeds.

The herbicidal rating is obtained by means of a fixed scale based on the percent inhibition of each plant species. The symbols in the Table are defined as follows:

| % Inhibition | Rating |
|---|---|
| 0-24 | 0 |
| 25-49 | 1 |
| 50-74 | 2 |
| 75-100 | 3 |
| Not planted | — |
| Species planted, no data | N |

WEED-PLANT HERBICIDE ACTIVITY

The plant species usually regarded as weeds which are utilized in one set of tests, the data for which are shown in Table 2, are identified by letter headings above the columns in accordance with the following legend:

A - Canada thistle*  E - Common Lambsquarters
B - Cocklebur  F - Pennsylvania Smartweed
C - Velvetleaf  G - Yellow Nutsedge*
D - Morningglory  H - Quackgrass*
I - Johnsongrass*
J - Downy Brome
K - Barnyardgrass

*Grown from vegetative propagules

TABLE 2

PRE-EMERGENT ACTIVITY FOR WEEDS

| Example No. | Kg/ha | A | B | C | D | E | F | G | H | I | J | K |
|---|---|---|---|---|---|---|---|---|---|---|---|---|
| 1 | 11.2 | — | 0 | 2 | 3 | 3 | 3 | 0 | 0 | 3 | 3 | 3 |
| 2 | 11.2 | — | 0 | 2 | 3 | 3 | 3 | 0 | 3 | 3 | 3 | 3 |
| 3 | 11.2 | — | 0 | 2 | 3 | 3 | 3 | 0 | 3 | 3 | 3 | 3 |
| 4 | 11.2 | — | 0 | 2 | 3 | 3 | 3 | 0 | 3 | 3 | 3 | 3 |
| 5 | 11.2 | — | 1 | 3 | 3 | 3 | 3 | 1 | 3 | 3 | 3 | 3 |
| 6 | 11.2 | — | 1 | 3 | 3 | 3 | 3 | 3 | 3 | 3 | 3 | 3 |
| 7 | 11.2 | — | 0 | 0 | 0 | 0 | 0 | 0 | 0 | 0 | 0 | 0 |
| 8 | 11.2 | — | 0 | 0 | 0 | 1 | 0 | 0 | 0 | 0 | 1 | 3 |
| 9 | 11.2 | — | 0 | 0 | 0 | 0 | 0 | 0 | 0 | 0 | 0 | 1 |
| 10 | 11.2 | — | 1 | 3 | 2 | 3 | 3 | 0 | 0 | 3 | 3 | 3 |
| 11 | 11.2 | — | 0 | 3 | 3 | 3 | 3 | 0 | 3 | 0 | 3 | 3 |
| 12 | 11.2 | — | 0 | 2 | 3 | 3 | 3 | 0 | 3 | 3 | 3 | 3 |
| 13 | 11.2 | — | 0 | 2 | 2 | 3 | 2 | 0 | 3 | 3 | 3 | 3 |
| 14 | 11.2 | 1 | 1 | 3 | 3 | 3 | 3 | 1 | 3 | 0 | 3 | 3 |
| 15 | 11.2 | — | 0 | 3 | 3 | 3 | 2 | 0 | 2 | 3 | 3 | 3 |
| 16 | 11.2 | — | 0 | 0 | 0 | 0 | 0 | 0 | 0 | 0 | 0 | 0 |
| 17 | 11.2 | — | 0 | 2 | 2 | 3 | 1 | 0 | 2 | 0 | 3 | 3 |
| 18 | 11.2 | — | 0 | 3 | 3 | 3 | 1 | 0 | 3 | 0 | 3 | 3 |
| 19 | 11.2 | — | 0 | 0 | 0 | 0 | 1 | 0 | 0 | 0 | 0 | 0 |
| 20 | 11.2 | — | 1 | 3 | 3 | 3 | 3 | 0 | 3 | 0 | 3 | 3 |
| 21 | 11.2 | — | 1 | 3 | 3 | 3 | 3 | 2 | 3 | 3 | 3 | 3 |
| 22 | 11.2 | — | 0 | 0 | 0 | 0 | 2 | 0 | 0 | N | 0 | 1 |
| 23 | 11.2 | — | 0 | 1 | 0 | 3 | 2 | 0 | 0 | N | 2 | 3 |
| 24 | 11.2 | — | 0 | 0 | 0 | 3 | 3 | 0 | 0 | N | 0 | 3 |
| 25 | 11.2 | — | 0 | 1 | 1 | 3 | 2 | 0 | 0 | 0 | 1 | 3 |
| 26 | 11.2 | — | 0 | 3 | 2 | 3 | 3 | 0 | 0 | 0 | 3 | 3 |
| 27 | 11.2 | 0 | 1 | 2 | 3 | 3 | 3 | 0 | 3 | 0 | 3 | 3 |
| 28 | 11.2 | — | 0 | 0 | 0 | 0 | 0 | 0 | 0 | 3 | 0 | 0 |
| 28* | 11.2 | — | 0 | 0 | 0 | 0 | 0 | 0 | 0 | 0 | 0 | 0 |
| 29 | 11.2 | — | 0 | 1 | 1 | 3 | 1 | 0 | 0 | 0 | 3 | 3 |
| 30 | 11.2 | — | 0 | 3 | 3 | 3 | 3 | 0 | 3 | 0 | 3 | 3 |
| 31 | 11.2 | — | 0 | 0 | 0 | 0 | 0 | 0 | 0 | 0 | 0 | 0 |

TABLE 2-continued
PRE-EMERGENT ACTIVITY FOR WEEDS

| Example No. | Kg/ha | A | B | C | D | E | F | G | H | I | J | K |
|---|---|---|---|---|---|---|---|---|---|---|---|---|
| 32 | 11.2 | — | 0 | 3 | 1 | 3 | 3 | 0 | 0 | 3 | 2 | 3 |
| 33 | 11.2 | — | 2 | 3 | 3 | 3 | 3 | 2 | 3 | 3 | 3 | 3 |
| 34 | 11.2 | — | 0 | 0 | 0 | 0 | 0 | 0 | 0 | N | 0 | 0 |
| 35 | 11.2 | — | 0 | 0 | 0 | 0 | 0 | 0 | 0 | 0 | 0 | 1 |
| 36 | 11.2 | — | 0 | 0 | 0 | 0 | 0 | 0 | 0 | N | 0 | 0 |
| 37 | 11.2 | — | 0 | 0 | 0 | 2 | 0 | 0 | 0 | 0 | 0 | 0 |
| 38 | 11.2 | 0 | 0 | 1 | 0 | 3 | 3 | 0 | 0 | 0 | 0 | 3 |
| 39 | 11.2 | 0 | 3 | 2 | 3 | 3 | 3 | 0 | 0 | 0 | 3 | 3 |
| 40 | 11.2 | 0 | 0 | 0 | 0 | 0 | 0 | 0 | 0 | 0 | 0 | 0 |
| 41 | 11.2 | 1 | 0 | 0 | 1 | 1 | 2 | 0 | 0 | 0 | 0 | 3 |
| 42 | 11.2 | — | 0 | 0 | 0 | 1 | 0 | 0 | 0 | 0 | 1 | 0 |
| 43 | 11.2 | — | 0 | 0 | 0 | 0 | 0 | 0 | 0 | 3 | 0 | 0 |
| 43* | 11.2 | — | 0 | 0 | 0 | 0 | 0 | 0 | 0 | 3 | 0 | 0 |
| 43* | 11.2 | 0 | 0 | 0 | 0 | 3 | 0 | 0 | 0 | 0 | 0 | 0 |
| 44 | 11.2 | 0 | 0 | 0 | 0 | 3 | 2 | 0 | 0 | 0 | 0 | 3 |
| 45 | 11.2 | 3 | 1 | 3 | 3 | 3 | 3 | 3 | 3 | 0 | 3 | 3 |
| 46 | 11.2 | 1 | 0 | 2 | 3 | 3 | 3 | 0 | 1 | 0 | 2 | 3 |
| 47 | 11.2 | 1 | 0 | 3 | 3 | 3 | 3 | 0 | 0 | 0 | 3 | 3 |
| 48 | 11.2 | 3 | 3 | 3 | 3 | 3 | 3 | 3 | 3 | 3 | 3 | 3 |
| 49 | 11.2 | 3 | 0 | 3 | 3 | 3 | 3 | 0 | 3 | 3 | 3 | 3 |
| 50 | 11.2 | 1 | 0 | 2 | 0 | 3 | 0 | 0 | 0 | 0 | 0 | 3 |
| 51 | 11.2 | 2 | 0 | 3 | 3 | 3 | 3 | 0 | 3 | 3 | 3 | 3 |
| 52 | 11.2 | 3 | 1 | 3 | 3 | 3 | 3 | 1 | 3 | 3 | 3 | 3 |
| 53 | 11.2 | 1 | 1 | 3 | 3 | 3 | 3 | 2 | 3 | 2 | 3 | 3 |
| 54 | 11.2 | 3 | 1 | 3 | 3 | 3 | 3 | 3 | 3 | 3 | 3 | 3 |
| 55 | 11.2 | 3 | 1 | 3 | 3 | 3 | 3 | 3 | 3 | 3 | 3 | 3 |
| 56 | 11.2 | 3 | 0 | 3 | 3 | 3 | 3 | 2 | 3 | 1 | 3 | 3 |
| 57 | 11.2 | 3 | 0 | 3 | 3 | 3 | 3 | 3 | 3 | 0 | 3 | 3 |
| 58 | 11.2 | 0 | 0 | 0 | 0 | 3 | 0 | 0 | 0 | N | 0 | 0 |
| 59 | 11.2 | 3 | 2 | 3 | 3 | 3 | 3 | 3 | 3 | 3 | 3 | 3 |
| 60 | 11.2 | 3 | 2 | 3 | 3 | 3 | 3 | 1 | 3 | 0 | 3 | 3 |
| 61 | 11.2 | 3 | 0 | 3 | 3 | 3 | 3 | 3 | 3 | 3 | 3 | 3 |
| 62 | 11.2 | 0 | 0 | 0 | 0 | 1 | 1 | 0 | 0 | 3 | 3 | 3 |
| 63 | 11.2 | 3 | 1 | 3 | 3 | 3 | 3 | 1 | 3 | 0 | 3 | 3 |
| 64 | 11.2 | 1 | 0 | 3 | 3 | 3 | 3 | 0 | 3 | 1 | 3 | 3 |
| 65 | 11.2 | 1 | 0 | 3 | 2 | 3 | 3 | 0 | 1 | 1 | 3 | 3 |
| 66 | 11.2 | 1 | 0 | 3 | 3 | 3 | 3 | 0 | 3 | 0 | 3 | 3 |
| 67 | 11.2 | 3 | 1 | 3 | 3 | 3 | 3 | 2 | 3 | 3 | N | 3 |
| 68 | 11.2 | 0 | 0 | 2 | 0 | 3 | 2 | 0 | 3 | 3 | 3 | 3 |
| 69 | 11.2 | 0 | 0 | 1 | 0 | 1 | 0 | 0 | 0 | 0 | 0 | 3 |
| 70 | 11.2 | 0 | 0 | 1 | 0 | 1 | 0 | 0 | 0 | 3 | 1 | 3 |
| 71 | 11.2 | 0 | 0 | 2 | 2 | 3 | 3 | 0 | 2 | 0 | 3 | 3 |
| 72 | 11.2 | 0 | 1 | 0 | 3 | 0 | 0 | 0 | 0 | 3 | 1 | 3 |
| 73 | 11.2 | 3 | 0 | 3 | 3 | 3 | 3 | 1 | 3 | 3 | — | 3 |
| 74 | 11.2 | 0 | 0 | 0 | 1 | 3 | 0 | 0 | 1 | 3 | 2 | 3 |
| 75 | 11.2 | 0 | 0 | 0 | 0 | 1 | 0 | 0 | 0 | N | 0 | 3 |
| 76 | 11.2 | 3 | 2 | 3 | 3 | 3 | 3 | 1 | 3 | 0 | — | 3 |
| 77 | 11.2 | 3 | 0 | 1 | 2 | 3 | 2 | 0 | 1 | 3 | — | 3 |
| 78 | 11.2 | 0 | 0 | 0 | 0 | 3 | 1 | 0 | 0 | 0 | — | 3 |
| 79 | 11.2 | 0 | 0 | 1 | 0 | 3 | 2 | 1 | 2 | 0 | — | 3 |
| 80 | 11.2 | 3 | 0 | 3 | 3 | 3 | 3 | 3 | 3 | 3 | N | 3 |

CROP AND WEED PLANT HERBICIDE ACTIVITY

The compounds were further tested by utilizing the above procedure on the following plant species i.e., on weeds in the presence of crop plants.

| | |
|---|---|
| L — Soybean | R — Hemp Sesbania |
| M — Sugarbeet | E — Common Lambsquarters |
| N — Wheat | F — Pennsylvania Smartweed |
| O — Rice | C — Velvetleaf |
| P — Grain Sorghum | J — Downy Brome |
| B — Cocklebur | S — Panicum spp. |
| Q — Wild Buckwheat | K — Barnyardgrass |
| D — Morningglory | T — Large Crabgrass |

The results are summarized in Table 3.

TABLE 3
PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 1 | 5.6 | 0 | 3 | 2 | 2 | 0 | 0 | 0 | 0 | 1 | 2 | 3 | 0 | 1 | 3 | 3 | 3 |
| | 1.12 | 0 | 0 | 0 | 0 | 0 | 0 | 0 | 0 | 0 | 0 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 2 | 5.6 | 0 | 3 | 2 | 3 | 3 | 0 | 2 | 2 | 2 | 3 | 3 | 2 | 3 | 3 | 3 | 3 |
| | 1.12 | 0 | 1 | 1 | 0 | 0 | 0 | 1 | 0 | 0 | 0 | 1 | 0 | 3 | 3 | 3 | 3 |
| | 0.28 | 0 | 1 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 3 | 5.6 | 0 | 3 | 3 | 2 | 3 | 0 | 2 | 0 | 1 | 3 | 3 | 0 | 3 | 3 | 3 | 3 |
| | 1.12 | 0 | 0 | 0 | 0 | 2 | 0 | 0 | 0 | 0 | 0 | 0 | 2 | 2 | 3 | 3 | 3 |
| | 0.28 | 0 | 0 | 0 | 0 | 0 | 0 | 1 | 0 | 0 | 0 | 0 | 1 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 4 | 5.6 | 0 | 3 | 0 | 1 | 3 | 0 | 3 | 3 | 1 | 3 | 3 | 1 | 3 | 3 | 3 | 3 |
| | 1.12 | 0 | 1 | 0 | 1 | 1 | 0 | 2 | 1 | 1 | 2 | 0 | 0 | 0 | 0 | 2 | 2 |
| | 0.28 | 0 | 0 | 0 | 0 | 0 | 0 | 0 | 0 | 0 | 0 | 0 | 0 | 0 | 0 | 0 | 0 |
| | 0.056 | 0 | 0 | 0 | 0 | 0 | 0 | 0 | 0 | 0 | 0 | 0 | 0 | 0 | 0 | 0 | 0 |
| 5 | 5.6 | 3 | 3 | 3 | 3 | 3 | 0 | 3 | 3 | 3 | 3 | 3 | 3 | 3 | 3 | 3 | 3 |
| | 1.12 | 0 | 2 | 2 | 1 | 3 | 0 | 0 | 1 | 2 | 2 | 3 | 1 | 3 | 3 | 3 | 3 |
| | 0.28 | 0 | 0 | 0 | 0 | 0 | 0 | 0 | 0 | 0 | 0 | 0 | 0 | 0 | 0 | 3 | 3 |
| | 0.056 | 0 | 0 | 0 | 0 | 0 | 0 | 0 | 0 | 0 | 0 | 0 | 0 | 0 | 0 | 0 | 2 |
| | 0.0112 | 0 | 0 | 0 | 0 | 0 | 0 | 0 | 0 | 0 | 0 | 0 | 0 | 0 | 0 | 0 | 0 |
| 6 | 5.6 | 3 | 3 | 3 | 3 | 3 | 2 | 3 | 3 | 3 | 3 | 3 | 3 | 3 | 3 | 3 | 3 |
| | 1.12 | 3 | 3 | 3 | 2 | 3 | 0 | 2 | 2 | 3 | 3 | 1 | 3 | 3 | 3 | 3 | 3 |
| | 0.28 | 0 | 1 | 1 | 1 | 2 | 0 | 0 | 0 | 1 | 1 | 1 | 3 | 3 | 3 | 3 | 3 |
| | 0.056 | 0 | 0 | 0 | 0 | 0 | 0 | 0 | 0 | 0 | 0 | 0 | 0 | 0 | 0 | 0 | 2 |
| | 0.0112 | 0 | 0 | 0 | 0 | 0 | 0 | 0 | 0 | 0 | 0 | 0 | 0 | 0 | 0 | 0 | 1 |
| 8 | 5.6 | 0 | 0 | 0 | 0 | 0 | 0 | 0 | 0 | 0 | 3 | 2 | 0 | 0 | 0 | 2 | 3 |
| | 1.12 | 0 | 0 | 0 | 0 | 0 | 0 | 0 | 0 | 0 | 0 | 0 | 0 | 0 | 0 | 0 | 0 |
| 10 | 5.6 | 0 | 0 | 1 | 1 | 1 | 0 | 2 | 0 | 2 | 3 | 2 | 0 | 1 | 2 | 3 | 3 |
| | 1.12 | 0 | 0 | 0 | 0 | 0 | 0 | N | 0 | 0 | 0 | 0 | 0 | 0 | 0 | 0 | 1 |
| | 0.28 | 0 | 0 | 0 | 0 | 0 | N | 1 | 0 | 0 | 0 | 0 | 0 | 0 | 0 | 0 | 1 |
| | 0.056 | 0 | 0 | 0 | 0 | 0 | N | 1 | 0 | 0 | 0 | 0 | 0 | 0 | 0 | 0 | 0 |
| 11 | 5.6 | 1 | 3 | 3 | 2 | 3 | 0 | 3 | 3 | 3 | 3 | 3 | 1 | 3 | 3 | 3 | 3 |
| | 1.12 | 0 | 0 | 0 | 0 | 3 | 0 | 2 | 0 | 1 | 1 | 0 | 3 | 3 | 3 | 3 | 3 |
| | 0.28 | 0 | 0 | 0 | 0 | 0 | N | 0 | 0 | 0 | 0 | 0 | 0 | 0 | 0 | 0 | 1 |
| | 0.056 | 0 | 0 | 0 | 0 | 0 | N | 0 | N | 0 | 0 | 0 | 0 | 0 | 0 | 0 | 0 |
| 12 | 5.6 | 1 | 1 | 3 | 2 | 3 | 0 | 2 | 2 | 2 | 2 | 3 | 1 | 3 | 3 | 3 | 3 |

TABLE 3-continued

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 1.12 | 1 | 0 | 0 | 1 | 1 | N | 3 | 0 | 1 | 0 | 0 | 0 | 3 | 3 | 3 | 3 |
| | 0.28 | 0 | 0 | 0 | 0 | 0 | N | 1 | 0 | 0 | 0 | 0 | 0 | 0 | 0 | 1 | 0 |
| | 0.056 | 0 | 0 | 0 | 1 | 0 | 0 | 0 | 0 | 0 | 0 | 0 | 0 | 0 | 0 | 0 | 0 |
| 13 | 5.6 | 0 | 0 | 0 | 1 | 3 | N | 2 | 1 | 1 | 3 | 2 | 0 | 3 | 2 | 3 | 3 |
| | 1.12 | 0 | 0 | 0 | 0 | 0 | N | 0 | 0 | 1 | 0 | 0 | 0 | 1 | 0 | 0 | 1 |
| | 0.28 | 0 | 0 | 0 | 0 | 0 | N | 0 | 0 | 0 | 0 | 0 | 0 | 0 | 0 | 0 | 0 |
| | 0.056 | 0 | 0 | 0 | 0 | 0 | N | N | 0 | 0 | 0 | 0 | 0 | 0 | 0 | 0 | 0 |
| 14 | 5.6 | 2 | 3 | 2 | 3 | 3 | 1 | 3 | 2 | 3 | 3 | 3 | 2 | 3 | 3 | 3 | 3 |
| | 1.12 | 0 | 0 | 0 | 1 | 3 | 1 | 0 | 1 | 2 | 2 | 1 | 0 | 2 | 3 | 3 | 3 |
| | 0.28 | 0 | 0 | 0 | 0 | 1 | 0 | 0 | 0 | 0 | 0 | 1 | 0 | 0 | 0 | 2 | 2 |
| | 0.056 | 0 | 0 | 0 | 0 | 0 | N | 0 | N | 0 | 0 | 0 | 0 | 0 | 0 | 0 | 0 |
| 15 | 5.6 | 0 | 0 | 1 | 2 | 3 | 0 | 3 | 0 | 2 | 2 | 2 | 0 | 3 | 3 | 3 | 3 |
| | 1.12 | 0 | 0 | 0 | 1 | 1 | N | 2 | 0 | 1 | 0 | 0 | 0 | 3 | 3 | 3 | 3 |
| | 0.28 | 0 | 0 | 0 | 0 | 0 | 0 | 0 | 0 | 0 | 0 | 0 | 0 | 0 | 0 | 0 | 2 |
| 17 | 5.6 | 0 | 1 | 0 | 0 | 0 | 0 | 2 | 0 | 0 | 3 | 2 | 1 | 2 | 1 | 2 | 3 |
| | 1.12 | 0 | 0 | 0 | 0 | 0 | 0 | 1 | 0 | 0 | 0 | 0 | 0 | 0 | 0 | 0 | 1 |
| | 0.28 | 0 | 0 | 0 | 0 | 0 | N | 0 | 0 | 0 | 0 | 0 | 0 | 0 | 0 | 0 | 0 |
| 18 | 5.6 | 0 | 0 | 0 | 1 | 3 | N | 2 | 2 | 1 | 3 | 2 | 2 | 3 | 3 | 3 | 3 |
| | 1.12 | 0 | 0 | 0 | 1 | 1 | N | 0 | 0 | 1 | 1 | 0 | 0 | 0 | 2 | 2 | 2 |
| | 0.28 | 0 | 0 | 0 | 0 | 0 | N | 1 | 0 | 0 | 0 | 0 | 0 | 0 | 0 | 0 | 0 |
| 20 | 5.6 | 1 | 3 | 1 | 2 | 3 | 0 | 3 | 2 | 3 | 3 | 3 | 3 | 3 | 3 | 3 | 3 |
| | 1.12 | 0 | 1 | 0 | 0 | 0 | 0 | 2 | 1 | 0 | 3 | 3 | 1 | 3 | 0 | 3 | 3 |
| | 0.28 | 0 | 0 | 0 | 0 | 0 | 0 | 0 | 0 | 0 | 3 | 1 | 0 | 1 | 1 | 0 | 2 |
| | 0.056 | 0 | 0 | 0 | 0 | 0 | 0 | 0 | 0 | 0 | 0 | 0 | 0 | 0 | 0 | 0 | 0 |
| 21 | 5.6 | 3 | 3 | 3 | 3 | 3 | 0 | 3 | 3 | 3 | 3 | 3 | 3 | 3 | 3 | 3 | 3 |
| | 1.12 | 2 | 3 | 3 | 1 | 2 | 0 | 3 | 3 | 3 | 3 | 3 | 3 | 3 | 3 | 3 | 3 |
| | 0.28 | 0 | 2 | 2 | 1 | 2 | 0 | 3 | 1 | 0 | 3 | 3 | 2 | 3 | 3 | 3 | 3 |
| | 0.056 | 0 | 0 | 0 | 0 | 0 | 0 | 0 | 0 | 0 | 2 | 2 | 1 | 1 | 0 | 2 | 3 |
| | 0.0112 | 0 | 0 | 1 | 0 | 0 | 0 | 0 | 0 | 0 | 2 | 2 | 1 | 0 | 0 | 0 | 2 |
| 23 | 5.6 | 0 | 0 | 0 | 1 | 0 | 0 | 0 | 0 | 0 | 2 | 1 | 0 | 2 | 1 | 2 | 2 |
| | 1.12 | 0 | 1 | 0 | 0 | 0 | 0 | 0 | 0 | 0 | 1 | 0 | 0 | 0 | 0 | 0 | 0 |
| | 0.28 | 0 | 0 | 0 | 0 | 0 | 0 | 0 | 0 | 0 | 0 | 0 | 0 | 0 | 0 | 0 | 0 |
| 24 | 5.6 | 0 | 0 | 0 | 1 | 1 | 0 | 1 | 0 | 0 | 2 | 1 | 0 | 0 | 1 | 3 | 3 |
| | 1.12 | 0 | 0 | 0 | 0 | 0 | 0 | 1 | 0 | 0 | 0 | 0 | 0 | 0 | 0 | 0 | 3 |
| | 0.28 | 0 | 0 | 0 | 0 | 0 | 0 | 0 | 0 | 0 | 0 | 0 | 0 | 0 | 0 | 0 | 1 |
| 25 | 5.6 | 0 | 0 | 0 | 0 | 1 | N | 1 | 0 | 0 | 2 | 1 | 0 | 0 | 0 | 0 | 3 |
| | 1.12 | 0 | 0 | 0 | 0 | 0 | N | N | N | 0 | 0 | 0 | 0 | 0 | 0 | 0 | 1 |
| | 0.28 | 0 | 0 | 0 | 0 | 0 | 0 | 0 | 0 | 0 | 0 | 0 | 0 | 0 | 0 | 0 | 0 |
| 26 | 5.6 | 0 | 1 | 0 | 3 | 3 | 0 | 2 | 2 | 2 | 3 | 2 | 1 | 3 | 3 | 3 | 3 |
| | 1.12 | 0 | 0 | 0 | 1 | 0 | 0 | 0 | 1 | 0 | 0 | 0 | 0 | 0 | 0 | 0 | 3 |
| | 0.28 | 0 | 0 | 0 | 1 | 0 | N | 0 | N | 0 | 0 | 0 | 0 | 0 | 0 | 0 | 1 |
| 27 | 5.6 | 2 | 3 | 3 | 3 | 3 | 0 | 3 | 3 | 3 | 3 | 3 | 2 | 3 | 3 | 3 | 3 |
| | 1.12 | 1 | 2 | 2 | 3 | 3 | 0 | 2 | 2 | 2 | 3 | 3 | 2 | 2 | 3 | 3 | 3 |
| | 0.28 | 0 | 0 | 0 | 3 | 1 | 0 | 0 | 0 | 2 | 1 | 2 | 0 | 0 | 3 | 3 | 3 |
| | 0.056 | 0 | 0 | 0 | 1 | 0 | 0 | 2 | 3 | 0 | 0 | 1 | 0 | 0 | 2 | 3 | 3 |
| | 0.0112 | 0 | 1 | 0 | 0 | 0 | 0 | 0 | 0 | 0 | 1 | 0 | 0 | 0 | 0 | 0 | 0 |
| 29 | 5.6 | 0 | 0 | 0 | 1 | 1 | 1 | 3 | 1 | 1 | 2 | 2 | 0 | 2 | 3 | 3 | 3 |
| | 1.12 | 0 | 0 | 0 | 1 | 0 | 0 | 2 | 0 | 0 | 0 | 0 | 0 | 0 | 1 | 2 | 3 |
| | 0.28 | 0 | 0 | 0 | 0 | 0 | 0 | 2 | 0 | 0 | 0 | 0 | 0 | 0 | 0 | 0 | 1 |
| 30 | 5.6 | 0 | 1 | 2 | 1 | 3 | 0 | 3 | 3 | 3 | 3 | 3 | 3 | 3 | 3 | 3 | 3 |
| | 1.12 | 0 | 1 | 0 | 2 | 2 | N | 3 | 0 | 0 | 3 | 2 | 0 | 3 | 3 | 3 | 3 |
| | 0.28 | 0 | 0 | 0 | 0 | 0 | 0 | 1 | 0 | 0 | 0 | 0 | 0 | 0 | 0 | 2 | 3 |
| | 0.056 | 0 | 0 | 0 | 0 | 0 | 0 | 0 | 0 | 0 | 0 | 0 | 0 | 0 | 0 | 0 | 1 |
| 32 | 5.6 | 0 | 3 | 1 | 0 | 1 | 0 | 3 | 2 | 2 | 3 | 3 | 2 | 3 | 3 | 3 | 3 |
| | 1.12 | 0 | 2 | 0 | 0 | 0 | 0 | 1 | 0 | 0 | 2 | 2 | 0 | 1 | 3 | 3 | 3 |
| | 0.28 | 0 | 2 | 0 | 0 | 0 | 0 | 0 | 0 | 0 | 1 | 1 | 1 | 2 | 1 | 2 | 1 |
| 33 | 5.6 | 3 | 3 | 3 | 3 | 3 | 0 | 3 | 3 | 3 | 3 | 3 | 3 | 3 | 3 | 3 | 3 |
| | 1.12 | 2 | 3 | 3 | 2 | 3 | 0 | 3 | 3 | 3 | 3 | 3 | 3 | 3 | 3 | 3 | 3 |
| | 0.28 | 0 | 3 | 3 | 0 | 2 | 0 | 3 | 2 | 1 | 3 | 3 | 0 | 3 | 3 | 3 | 3 |
| | 0.056 | 0 | 1 | 0 | 0 | 0 | 0 | 0 | 0 | 0 | 3 | 2 | 0 | 0 | 1 | 3 | 3 |
| | 0.0112 | 0 | 0 | 0 | 0 | 0 | 0 | 0 | 0 | 0 | 0 | 0 | 0 | 0 | 0 | 0 | 1 |
| 38 | 5.6 | 0 | 0 | 0 | 1 | 2 | 3 | 1 | 2 | 1 | 2 | 3 | 1 | 3 | 3 | 3 | 3 |
| | 1.12 | 0 | 0 | 0 | 1 | 1 | 0 | 1 | 0 | 1 | 2 | 3 | 0 | 3 | 3 | 3 | 3 |
| | 0.28 | 0 | 0 | 0 | 0 | 1 | 0 | 0 | 0 | 0 | 0 | 3 | 0 | 1 | 3 | 3 | 3 |
| | 0.056 | 0 | 0 | 0 | 0 | 0 | 0 | 0 | 0 | 0 | 0 | 0 | 0 | 0 | 0 | 0 | 0 |
| | 0.0112 | 0 | 0 | 0 | 0 | 1 | 0 | 0 | 0 | 0 | 0 | 0 | 0 | 0 | 0 | 0 | 1 |
| 39 | 5.6 | 1 | 1 | 2 | 3 | 3 | 0 | 2 | 2 | 2 | 3 | 3 | 2 | 3 | 3 | 3 | 3 |
| | 1.12 | 0 | 1 | 1 | 2 | 3 | 0 | 2 | 2 | 2 | 2 | 2 | 1 | 3 | 3 | 3 | 3 |
| | 0.28 | 0 | 1 | 0 | 1 | 0 | 0 | 1 | 1 | 0 | 2 | 2 | 0 | 3 | 3 | 3 | 3 |
| | 0.056 | 0 | 0 | 0 | 0 | 0 | 0 | 1 | 1 | 0 | 0 | 0 | 0 | 1 | 0 | 2 | 3 |
| | 0.0112 | 0 | 0 | 0 | 1 | 0 | 0 | 1 | 0 | 1 | 1 | 0 | 0 | 0 | 1 | 0 | 0 |
| 41 | 5.6 | 0 | 0 | 0 | 0 | 0 | N | 1 | 2 | 0 | 1 | 2 | 1 | 2 | 3 | 3 | 3 |
| | 1.12 | 0 | 0 | 0 | 0 | 0 | 0 | 0 | 0 | 0 | 0 | 1 | 0 | 1 | 3 | 3 | 3 |
| | 0.28 | 0 | 1 | 0 | 0 | 0 | 0 | 1 | 0 | 0 | 0 | 0 | 1 | 0 | 1 | 3 | 3 |
| | 0.056 | 0 | 1 | 0 | 0 | 0 | 0 | 0 | 0 | 0 | 0 | N | 0 | 0 | 0 | 0 | 0 |
| 44 | 5.6 | 0 | 1 | 0 | 0 | 1 | 0 | 0 | 0 | 0 | 1 | 1 | 0 | 0 | 3 | 3 | 3 |
| | 1.12 | 0 | 0 | 0 | 0 | 0 | 0 | 0 | 0 | 0 | 0 | 0 | 0 | 0 | 1 | 3 | 3 |
| | 0.28 | 0 | 1 | 0 | 0 | 0 | 0 | 0 | 0 | 0 | 0 | 0 | 0 | 0 | 1 | 0 | 0 |
| | 0.056 | 0 | 0 | 0 | 0 | 0 | 0 | 0 | 0 | 0 | 0 | 0 | 0 | 0 | 0 | 0 | 0 |
| 45 | 5.6 | 2 | 3 | 2 | 3 | 3 | 0 | 3 | 3 | 2 | 3 | 3 | 1 | 3 | 3 | 3 | 3 |

TABLE 3-continued

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| | 1.12 | 1 | 1 | 2 | 3 | 3 | 0 | 1 | 2 | 1 | 2 | 2 | 1 | 3 | 3 | 3 | 3 |
| | 0.28 | 0 | 0 | 0 | 2 | 0 | 0 | 0 | 0 | 0 | 0 | 2 | 0 | 0 | 1 | 3 | 2 |
| | 0.056 | 0 | 0 | 0 | 1 | 0 | 0 | 0 | 0 | 0 | 0 | 1 | 0 | 0 | 0 | 1 | 1 |
| | 0.0112 | 0 | 0 | 0 | 1 | 0 | 0 | 0 | 0 | 0 | 0 | 1 | 0 | 0 | 1 | 1 | 1 |
| 46 | 5.6 | 2 | 2 | 0 | 3 | 3 | 0 | 3 | 3 | 2 | 3 | 3 | 2 | 3 | 3 | 3 | 3 |
| | 1.12 | 0 | 1 | 0 | 2 | 2 | 0 | 2 | 2 | 1 | 2 | 2 | 1 | 3 | 3 | 3 | 3 |
| | 0.28 | 0 | 0 | 0 | 0 | 1 | N | 0 | 0 | 1 | 2 | 1 | 0 | 0 | 2 | 3 | 3 |
| | 0.056 | 0 | 0 | 0 | 0 | 0 | 0 | 1 | 0 | 0 | 0 | 0 | 0 | 0 | 0 | 0 | 0 |
| | 0.0112 | 0 | 0 | 0 | 0 | 0 | 0 | 0 | 0 | 0 | 0 | 0 | 0 | 0 | 0 | 0 | 0 |
| 47 | 5.6 | 1 | 2 | 0 | 3 | 2 | 0 | 3 | 2 | 2 | 3 | 3 | 0 | 3 | 3 | 3 | 3 |
| | 1.12 | 0 | 0 | 0 | 2 | 1 | 0 | 3 | 1 | 1 | 2 | 2 | 0 | 2 | 3 | 3 | 3 |
| | 0.28 | 0 | 0 | 0 | 1 | 0 | 0 | 0 | 0 | 0 | 0 | 1 | 0 | 0 | 1 | 2 | 3 |
| | 0.056 | 0 | 1 | 0 | 0 | 0 | 0 | 0 | 0 | 0 | 0 | 0 | 0 | 1 | 0 | 0 | 0 |
| 48 | 5.6 | 3 | 3 | 3 | 3 | 3 | 2 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 1 | 1 | 3 | 3 | 3 | 0 | 2 | 2 | 2 | 3 | 2 | 1 | 3 | 3 | 3 | 3 |
| | 0.056 | 0 | 0 | 0 | 3 | 1 | 0 | 2 | 1 | 2 | 2 | 1 | 1 | 2 | 3 | 3 | 3 |
| | 0.0112 | 0 | 0 | 0 | 2 | 1 | 0 | N | 1 | 1 | 1 | 0 | 1 | 0 | 2 | 2 | 2 |
| 49 | 5.6 | 3 | 3 | 3 | 3 | 3 | 0 | 3 | 3 | 2 | 3 | 3 | 2 | 3 | 3 | 3 | 3 |
| | 1.12 | 1 | 3 | 2 | 3 | 3 | 0 | 3 | 2 | 2 | 3 | 2 | 1 | 3 | 3 | 3 | 3 |
| | 0.28 | 0 | 2 | 0 | 1 | 0 | 0 | 1 | 2 | 1 | 3 | 2 | 1 | 1 | 3 | 3 | 3 |
| | 0.056 | 0 | 0 | 0 | 1 | 0 | 0 | 1 | 0 | 0 | 3 | 0 | 0 | 0 | 3 | 3 | 3 |
| | 0.0112 | 0 | 1 | 0 | 0 | 0 | 0 | N | 0 | 0 | 2 | 0 | 0 | 0 | 0 | 0 | 2 |
| 50 | 5.6 | 0 | 2 | 0 | 1 | 0 | 0 | 0 | 2 | 1 | 0 | 1 | 0 | 0 | 3 | 3 | 3 |
| | 1.12 | 0 | 0 | 0 | 1 | 0 | 0 | 0 | 1 | 0 | 0 | 0 | 0 | 0 | 1 | 3 | 3 |
| | 0.28 | 0 | 1 | 0 | 0 | 0 | 0 | 2 | 1 | 0 | 1 | 0 | 0 | 2 | 2 | 0 | 0 |
| | 0.056 | 0 | 0 | 0 | 0 | 0 | 0 | 0 | 0 | 0 | 0 | 0 | 0 | 0 | 0 | 0 | 0 |
| 51 | 5.6 | 2 | 3 | 3 | 3 | 3 | 0 | 3 | 2 | 3 | 3 | 3 | 2 | 3 | 3 | 3 | 3 |
| | 1.12 | 0 | 0 | 2 | 1 | 3 | 0 | 2 | 0 | 2 | 3 | 2 | 0 | 3 | 3 | 3 | 3 |
| | 0.28 | 0 | 0 | 0 | 0 | 0 | 0 | 1 | 0 | 1 | 0 | 0 | 0 | 1 | 2 | 3 | 3 |
| | 0.056 | 0 | 0 | 0 | 0 | 0 | 0 | 0 | 0 | 0 | 0 | 0 | 0 | 0 | 0 | 0 | 1 |
| 52 | 5.6 | 2 | 3 | 3 | 3 | 3 | 0 | 3 | 3 | 3 | 3 | 3 | 3 | 3 | 3 | 3 | 3 |
| | 1.12 | 0 | 2 | 2 | 2 | 2 | 0 | 3 | 1 | 2 | 3 | 2 | 2 | 2 | 3 | 3 | 3 |
| | 0.28 | 0 | 1 | 0 | 0 | 0 | 0 | 2 | 1 | 1 | 3 | 1 | 0 | 0 | 3 | 3 | 3 |
| | 0.056 | 0 | 0 | 0 | 0 | 1 | 0 | 2 | 0 | 1 | 1 | 0 | 0 | 0 | 2 | 1 | 2 |
| 53 | 5.6 | 2 | 3 | 3 | 3 | 3 | 0 | 3 | 3 | 3 | 3 | 3 | 2 | 3 | 3 | 3 | 3 |
| | 1.12 | 0 | 2 | 1 | 2 | 3 | 0 | 3 | 2 | 2 | 3 | 1 | 2 | 3 | 3 | 3 | 3 |
| | 0.28 | 0 | 0 | 0 | 1 | 2 | 0 | 3 | 0 | 0 | 2 | 0 | 2 | 2 | 2 | 3 | 3 |
| | 0.056 | 0 | 0 | 0 | 0 | 1 | 0 | 2 | 0 | 0 | 1 | 0 | 1 | 0 | 1 | 1 | 3 |
| | 0.0112 | 0 | 0 | 0 | 0 | 0 | 0 | 0 | 0 | 0 | 0 | 0 | 0 | 0 | 0 | 0 | 2 |
| 54 | 5.6 | 3 | 3 | 3 | 3 | 3 | 0 | 3 | 3 | 3 | 3 | 3 | 3 | 3 | 3 | 3 | 3 |
| | 1.12 | 3 | 2 | 3 | 3 | 3 | 0 | 3 | 2 | 3 | 3 | 3 | 2 | 3 | 3 | 3 | 3 |
| | 0.28 | 0 | 0 | 1 | 2 | 2 | 0 | 1 | 1 | 1 | 3 | 1 | 0 | 3 | 3 | 3 | 3 |
| | 0.056 | 0 | 0 | 0 | 0 | 0 | 0 | 0 | 0 | 0 | 0 | 0 | 0 | 1 | 1 | 2 | 1 |
| | 0.0112 | 0 | 0 | 0 | 0 | 0 | 0 | 0 | 0 | 0 | 0 | 0 | 0 | 0 | 0 | 0 | 0 |
| 55 | 5.6 | 3 | 3 | 3 | 3 | 3 | 1 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 3 | 3 | 3 | 3 | 3 |
| | 0.28 | 1 | 2 | 2 | 1 | 3 | 0 | 3 | 2 | 2 | 3 | 3 | 2 | 3 | 3 | 3 | 3 |
| | 0.056 | 0 | 0 | 0 | 1 | 3 | 0 | 2 | 1 | 1 | 2 | 1 | 0 | 3 | 3 | 3 | 3 |
| | 0.0112 | 0 | 0 | 0 | 0 | 1 | 0 | 0 | 0 | 0 | 0 | 0 | 0 | 0 | 1 | 1 | 3 |
| 56 | 5.6 | 3 | 3 | 3 | 3 | 3 | 0 | 3 | 3 | 2 | 3 | 3 | 3 | 3 | 3 | 3 | 3 |
| | 1.12 | 2 | 3 | 3 | 2 | 3 | 0 | 3 | 2 | 2 | 3 | 3 | 2 | 3 | 3 | 3 | 3 |
| | 0.28 | 0 | 1 | 1 | 1 | 3 | 0 | 3 | 0 | 2 | 3 | 1 | 0 | 3 | 3 | 3 | 3 |
| | 0.056 | 0 | 0 | 0 | 0 | 1 | 0 | 1 | 0 | 0 | 2 | 0 | 0 | 1 | 2 | 2 | 2 |
| | 0.0112 | 0 | 0 | 0 | 0 | 0 | 0 | 1 | 0 | 0 | 1 | 0 | 0 | 0 | 0 | 0 | 1 |
| 57 | 5.6 | 3 | 3 | 3 | 3 | 3 | 0 | 3 | 3 | 2 | 3 | 3 | 3 | 3 | 3 | 3 | 3 |
| | 1.12 | 0 | 1 | 0 | 2 | 2 | 0 | 1 | 3 | 2 | 3 | 2 | 1 | 3 | 3 | 3 | 3 |
| | 0.28 | 0 | 0 | 0 | 1 | 2 | 0 | 1 | 2 | 0 | 2 | 1 | 0 | 1 | 3 | 3 | 3 |
| | 0.056 | 0 | 0 | 0 | 0 | 0 | 0 | 1 | 0 | 1 | 0 | 0 | 0 | 0 | 1 | 1 | 2 |
| | 0.0112 | 0 | 0 | 0 | 0 | 0 | 0 | 0 | 0 | 0 | 0 | 0 | 0 | 0 | 0 | 0 | 0 |
| 59 | 5.6 | 3 | 3 | 3 | 3 | 3 | 1 | 3 | 3 | 3 | 3 | 3 | 3 | 3 | 3 | 3 | 3 |
| | 1.12 | 3 | 3 | 3 | 3 | 3 | 0 | 3 | 3 | 3 | 3 | 3 | 2 | 3 | 3 | 3 | 3 |
| | 0.28 | 1 | 3 | 3 | 1 | 3 | 0 | 2 | 3 | 2 | 3 | 3 | 1 | 3 | 3 | 3 | 3 |
| | 0.056 | 0 | 1 | 1 | 0 | 2 | 0 | 0 | 0 | 0 | 0 | 0 | 0 | 2 | 3 | 3 | 3 |
| | 0.0112 | 0 | 0 | 0 | 0 | 0 | 0 | 0 | 0 | 0 | 0 | 0 | 0 | 0 | 1 | 0 | 0 |
| 60 | 5.6 | 3 | 3 | 3 | 3 | 3 | 0 | 3 | 3 | 3 | 3 | 3 | 3 | 3 | 3 | 3 | 3 |
| | 1.12 | 0 | 2 | 3 | 3 | 3 | 0 | 2 | 2 | 2 | 3 | 3 | 2 | 3 | 3 | 3 | 3 |
| | 0.28 | 0 | 0 | 2 | 1 | 3 | 0 | 1 | 1 | 0 | 3 | 1 | 0 | 3 | 3 | 3 | 3 |
| | 0.056 | 0 | 0 | 0 | 0 | 1 | 0 | 0 | 0 | 0 | 2 | 1 | 0 | 1 | 1 | 1 | 2 |
| 61 | 5.6 | 3 | 3 | 3 | 3 | 3 | 1 | 3 | 3 | 3 | 3 | 3 | 3 | 3 | 3 | 3 | 3 |
| | 1.12 | 3 | 3 | 3 | 3 | 3 | 1 | 3 | 3 | 3 | 3 | 3 | 3 | 3 | 3 | 3 | 3 |
| | 0.56 | 2 | 3 | 2 | 2 | 2 | 0 | 1 | 3 | 3 | 3 | 3 | 2 | 3 | 3 | 3 | 3 |
| | 0.28 | 0 | 2 | 1 | 2 | 3 | 1 | 2 | 3 | 3 | 3 | 3 | 2 | 3 | 3 | 3 | 3 |
| | 0.14 | 2 | 2 | 1 | 1 | 2 | 0 | 2 | 2 | 3 | 3 | 3 | 2 | 3 | 3 | 3 | 3 |
| | 0.07 | 1 | 2 | 0 | 0 | 1 | 0 | 1 | 1 | 1 | 2 | 3 | 0 | 0 | 2 | 3 | 3 |
| | 0.035 | 0 | 1 | 0 | 1 | 1 | 0 | 0 | 0 | 1 | 1 | 2 | 0 | 1 | 3 | 3 | 3 |
| 62 | 5.6 | 1 | 2 | 3 | 0 | 3 | 0 | 3 | 2 | 0 | 3 | 3 | 0 | 3 | 3 | 3 | 3 |
| | 1.12 | 0 | 2 | 1 | 1 | 0 | 0 | 1 | 1 | 1 | 3 | 0 | 0 | 2 | 2 | 3 | 3 |
| | 0.56 | 0 | 0 | 0 | 0 | 0 | 0 | 0 | 0 | 0 | 0 | 0 | 1 | 1 | 0 | 1 | 1 |
| | 0.28 | 0 | 0 | 0 | 0 | 0 | 0 | 0 | 0 | 0 | 0 | 0 | 0 | 0 | 0 | 0 | 0 |

TABLE 3-continued

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 63 | 5.6 | 3 | 3 | 3 | 3 | 3 | 1 | 3 | 3 | 3 | 3 | 3 | 3 | 3 | 3 | 3 | 3 |
|  | 1.12 | 2 | 3 | 2 | 2 | 3 | 0 | 3 | 1 | 2 | 3 | 3 | 2 | 3 | 3 | 3 | 3 |
|  | 0.56 | 1 | 1 | 1 | 1 | 2 | 0 | 1 | 0 | 1 | 2 | 3 | 0 | 2 | 3 | 3 | 3 |
|  | 0.28 | 0 | 0 | 0 | 0 | 1 | 0 | 1 | 0 | 0 | 0 | 0 | 0 | 1 | 0 | 1 | 3 |
|  | 0.14 | 0 | 0 | 0 | 0 | 0 | 0 | 0 | 0 | 0 | 0 | 0 | 0 | 0 | 0 | 0 | 1 |
|  | 0.07 | 0 | 0 | 0 | 0 | 0 | 0 | 0 | 0 | 0 | 0 | 0 | 0 | 0 | 0 | 0 | 0 |
| 64 | 5.6 | 3 | 3 | 3 | 2 | 3 | 0 | 3 | 2 | 3 | 3 | 3 | 3 | 3 | 3 | 3 | 3 |
|  | 1.12 | 0 | 1 | 1 | 0 | 3 | 0 | 2 | 1 | 1 | 3 | 3 | 2 | 2 | 3 | 3 | 3 |
|  | 0.56 | 0 | 0 | 0 | 0 | 1 | 0 | 0 | 0 | 1 | 3 | 2 | 1 | 1 | 2 | 3 | 3 |
|  | 0.28 | 0 | 0 | 0 | 0 | 0 | 0 | 0 | 0 | 0 | 2 | 1 | 1 | 0 | 1 | 3 | 3 |
|  | 0.14 | 0 | 0 | 0 | 0 | 0 | 0 | 0 | 0 | 0 | 1 | 1 | 0 | 0 | 0 | 2 | 3 |
|  | 0.07 | 0 | 0 | 0 | 0 | 0 | 0 | 0 | 0 | 0 | 1 | 1 | 0 | 0 | 0 | 0 | 3 |
| 65 | 5.6 | 0 | 2 | 0 | 1 | 3 | 0 | 3 | 0 | 2 | 3 | 3 | 1 | 1 | 3 | 3 | 3 |
|  | 1.12 | 0 | 3 | 0 | 0 | 1 | 0 | 3 | 0 | 0 | 2 | 2 | 0 | 2 | 3 | 3 | 3 |
|  | 0.56 | 0 | 0 | 0 | 0 | 0 | 0 | 0 | 0 | 0 | 1 | 1 | 0 | 0 | 0 | 0 | 3 |
|  | 0.28 | 0 | 0 | 0 | 0 | 0 | 0 | 0 | 0 | 0 | 0 | 0 | 0 | 0 | 0 | 0 | 1 |
|  | 0.14 | 0 | 0 | 0 | 0 | 0 | 0 | 0 | 0 | 0 | 0 | 0 | 0 | 0 | 0 | 0 | 0 |
|  | 0.07 | 0 | 0 | 0 | 0 | 0 | 0 | 0 | 0 | 0 | 0 | 0 | 0 | 0 | 0 | 0 | 0 |
| 66 | 5.6 | 0 | 2 | 0 | 1 | 3 | 0 | 3 | 1 | 2 | 3 | 3 | 1 | 1 | 3 | 3 | 3 |
|  | 1.12 | 0 | 1 | 0 | 1 | 1 | 0 | 1 | 0 | 0 | 1 | 1 | 0 | 0 | 1 | 3 | 3 |
|  | 0.56 | 0 | 0 | 0 | 0 | 0 | 0 | 0 | 0 | 0 | 0 | 0 | 0 | 0 | 1 | 1 | 2 |
|  | 0.28 | 0 | 0 | 0 | 0 | 0 | 0 | 1 | 0 | 0 | 0 | 0 | 0 | 0 | 2 | 0 | 0 |
|  | 0.14 | 0 | 0 | 0 | 0 | 0 | 0 | 0 | 0 | 0 | 0 | 0 | 0 | 0 | 0 | 0 | 0 |
|  | 0.07 | 0 | 0 | 0 | 0 | 0 | 0 | 0 | 0 | 0 | 0 | 0 | 0 | 0 | 0 | 0 | 0 |
| 67 | 5.6 | 3 | 3 | 2 | 3 | 3 | 0 | 3 | 3 | 3 | 3 | 3 | 3 | 3 | 3 | 3 | 3 |
|  | 1.12 | 1 | 3 | 1 | 2 | 2 | 2 | 3 | 3 | 3 | 3 | 3 | 3 | 3 | 3 | 3 | 3 |
|  | 0.56 | 0 | 3 | 1 | 2 | 3 | 0 | 2 | 3 | 3 | 3 | 3 | 1 | 2 | 3 | 3 | 3 |
|  | 0.28 | 1 | 2 | 1 | 1 | 1 | 0 | 1 | 1 | 1 | 0 | 3 | 1 | 0 | 3 | 3 | 3 |
|  | 0.14 | 0 | 0 | 0 | 0 | 0 | 0 | 0 | 0 | 1 | 1 | 0 | 0 | 2 | 3 | 3 | 3 |
|  | 0.07 | 0 | 0 | 0 | 1 | 0 | 0 | 0 | 0 | 0 | 1 | 0 | 0 | 1 | 2 | 3 | 3 |
|  | 0.035 | 0 | 0 | 0 | 0 | 0 | 0 | 1 | 0 | 0 | 0 | 0 | 0 | 0 | 0 | 1 | 2 |
|  | 0.0182 | 0 | 0 | 0 | 0 | 0 | 0 | 0 | 0 | 1 | 0 | 0 | 0 | 0 | 1 | 0 | 1 |
|  | 0.009 | 0 | 0 | 0 | 0 | 0 | 0 | 0 | 0 | 0 | 0 | 0 | 0 | 0 | 0 | 0 | 0 |
| 68 | 5.6 | 1 | 3 | 3 | 3 | 3 | 0 | 1 | 1 | 2 | 3 | 3 | 2 | 3 | 3 | 3 | 3 |
|  | 1.12 | 0 | 0 | 0 | 0 | 0 | 0 | 0 | 0 | 0 | 0 | 0 | 0 | 2 | 2 | 2 | 3 |
|  | 0.56 | 0 | 0 | 0 | 1 | 0 | 0 | 0 | 0 | 0 | 0 | 0 | 0 | 0 | 0 | 1 | 2 |
|  | 0.28 | 0 | 0 | 0 | 0 | 0 | 0 | 0 | 0 | 0 | 0 | 1 | 0 | 0 | 0 | 0 | 1 |
|  | 0.24 | N | 0 | 0 | 0 | 0 | 0 | 0 | 0 | 0 | 0 | 0 | 0 | 0 | 0 | 0 | 0 |
|  | 0.07 | 0 | 0 | 0 | 0 | 0 | 0 | 0 | 0 | 0 | 0 | 0 | 0 | 0 | 0 | 0 | 0 |
| 69 | 5.6 | 0 | 2 | 0 | 0 | 3 | 0 | 1 | 3 | 2 | 3 | 3 | 2 | 2 | 3 | 3 | 3 |
|  | 1.12 | 0 | 0 | 0 | 0 | 0 | 0 | 1 | 1 | 1 | 2 | 1 | 0 | 1 | 2 | 1 | 1 |

POST-EMERGENT HERBICIDE EXAMPLES

The post-emergence herbicidal activity of some of the various compounds of this invention was demonstrated by greenhouse testing in the following manner. Top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan, is removed individually to a spraying chamber and sprayed by means of an atomizer, operating at a spray pressure of 170.3 kPa (10 psig) at the application rates noted. In the spray solution is an amount of an emulsifying agent mixture to give a spray solution or suspension which contains about 0.4% by volume of the emulsifier. The spray solution or suspension contains a sufficient amount of the candidate chemical in order to give application rates of the active ingredient corresponding to those shown in Tables while applying a total amount of solution or suspension equivalent to 1870 L/Ha (200 gallons/acre). The pans were returned to the greenhouse and watered as before and the injury to the plants as compared to the control is observed at approximately 10–14 days (usually 11 days) and in some instances observed again at 24–28 days (usually 25 days) after spraying. These latter observations are designated by an asterisk (*) following the column of examples numbers in the Table.

The post-emergent herbicidal activity index used in Table 4 is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — |
| Species planted, no data | N |

TABLE 4

POST-EMERGENT ACTIVITY FOR WEEDS

| Example No. | Kg/ha | A | B | C | D | E | F | G | H | I | J | K |
|---|---|---|---|---|---|---|---|---|---|---|---|---|
| 1 | 11.2 | — | 0 | 0 | 0 | 0 | 0 | 0 | 0 | 0 | 0 | 0 |
| 2 | 11.2 | — | 0 | 0 | 0 | 0 | 0 | 0 | 0 | N | 0 | 0 |
| 3 | 11.2 | — | 0 | 0 | 0 | 0 | 0 | 0 | 0 | 0 | 0 | 0 |
| 4 | 11.2 | — | 0 | 0 | 1 | 0 | 0 | 0 | 0 | 0 | 0 | 0 |
| 5 | 11.2 | — | N | 1 | 1 | 0 | 0 | 0 | 0 | 0 | 0 | 0 |
| 6 | 11.2 | — | 0 | 0 | 0 | 0 | 0 | 0 | 0 | 0 | 0 | 1 |
| 7 | 11.2 | — | 0 | 0 | 0 | 0 | 0 | 0 | 0 | 0 | 0 | 0 |
| 8 | 11.2 | 0 | 0 | 0 | 0 | 0 | 0 | 0 | 0 | 0 | 0 | 0 |
| 9 | 11.2 | — | 0 | 0 | 0 | 0 | 0 | 0 | 0 | 0 | 0 | 0 |

TABLE 4-continued
POST-EMERGENT ACTIVITY FOR WEEDS

| Example No. | Kg/ha | A | B | C | D | E | F | G | H | I | J | K |
|---|---|---|---|---|---|---|---|---|---|---|---|---|
| 10 | 11.2 | — | 0 | 0 | 0 | 1 | 0 | 0 | 0 | 0 | 0 | 0 |
| 11 | 11.2 | — | 0 | 0 | 0 | 0 | 0 | 0 | 0 | 0 | 0 | 0 |
| 12 | 11.2 | — | 0 | 0 | 0 | 0 | 0 | 0 | 0 | 0 | 0 | 0 |
| 13 | 11.2 | — | 0 | 0 | 0 | 0 | 0 | 0 | 0 | 0 | 0 | 1 |
| 14 | 11.2 | — | 1 | 1 | 0 | 0 | 0 | 0 | 0 | N | 1 | 0 |
| 15 | 11.2 | — | 0 | 0 | 0 | 0 | 0 | 0 | 0 | 0 | 0 | 0 |
| 16 | 11.2 | — | 0 | 0 | 0 | 0 | 0 | 0 | 0 | 0 | 0 | 0 |
| 17 | 11.2 | — | 0 | 0 | 0 | 0 | 0 | 0 | 0 | 0 | 0 | 0 |
| 18 | 11.2 | — | 0 | 0 | 0 | 1 | 0 | 0 | 0 | 0 | 0 | 0 |
| 19 | 11.2 | — | 0 | 0 | 0 | 0 | 0 | 0 | 0 | 0 | 0 | 0 |
| 20 | 11.2 | — | 0 | 0 | 0 | 1 | 0 | 0 | 0 | 0 | 0 | 0 |
| 21 | 11.2 | — | 0 | 1 | 1 | 0 | 0 | 0 | 0 | 0 | 1 | 0 |
| 22 | 11.2 | — | 0 | 0 | 0 | 0 | 0 | 0 | 0 | 0 | 0 | 0 |
| 23 | 11.2 | — | 0 | 1 | 0 | 0 | 0 | 0 | 0 | N | 0 | 0 |
| 24 | 11.2 | — | 0 | 0 | 0 | 0 | 0 | 0 | 0 | N | 0 | 0 |
| 25 | 11.2 | — | 0 | 0 | 0 | 0 | 0 | 0 | 0 | 0 | 0 | 0 |
| 26 | 11.2 | — | 0 | 0 | 0 | 0 | 0 | 0 | 0 | 0 | 0 | 0 |
| 27 | 11.2 | — | 0 | 0 | 0 | 0 | 0 | 0 | 0 | N | 0 | 0 |
| 28 | 11.2 | — | 0 | 0 | 0 | N | 0 | 0 | 0 | 0 | 0 | 0 |
| 29 | 11.2 | — | 0 | 0 | 0 | 0 | 0 | 0 | 0 | 0 | 0 | 0 |
| 30 | 11.2 | — | 1 | 1 | 0 | 0 | 0 | 0 | 0 | 0 | 0 | 0 |
| 31 | 11.2 | — | 0 | 0 | 0 | 0 | 0 | 0 | 0 | 0 | 0 | 0 |
| 32 | 11.2 | — | 1 | 1 | 1 | 1 | 0 | 0 | 0 | 0 | 0 | 0 |
| 33 | 11.2 | — | 1 | 1 | 1 | 0 | 1 | 0 | 0 | 0 | 0 | 0 |
| 34 | 11.2 | — | 0 | 0 | 0 | 0 | 0 | 0 | 0 | N | 0 | 0 |
| 35 | 11.2 | — | 0 | 0 | 0 | 0 | 0 | 0 | 0 | N | 0 | 0 |
| 36 | 11.2 | — | 0 | 0 | 0 | 0 | 0 | 0 | 0 | N | 0 | 0 |
| 37 | 11.2 | — | 0 | 0 | 0 | 0 | 0 | 0 | 0 | 0 | 0 | 0 |
| 38 | 11.2 | — | 1 | 0 | 1 | 0 | 0 | 1 | 0 | N | 1 | 0 |
| 39 | 11.2 | 0 | 0 | 1 | 0 | 0 | 0 | 0 | 0 | 0 | 0 | 0 |
| 40 | 11.2 | 0 | 0 | 0 | 0 | N | 0 | 0 | 0 | 0 | 0 | 0 |
| 41 | 11.2 | 0 | 0 | 1 | 1 | 0 | 0 | 0 | 0 | 0 | 0 | 0 |
| 42 | 11.2 | — | 0 | 0 | 0 | 0 | 0 | 0 | 0 | 0 | 0 | 1 |
| 43 | 11.2 | — | 0 | 0 | 0 | 0 | 0 | 0 | 0 | 0 | 0 | 0 |
| 44 | 11.2 | 0 | 0 | 1 | 1 | 0 | 0 | 0 | 0 | 0 | 0 | 0 |
| 45 | 11.2 | — | 0 | 0 | 0 | 0 | 0 | 0 | 0 | 0 | 0 | 0 |
| 46 | 11.2 | 0 | 0 | 1 | 1 | 1 | 0 | 0 | 0 | 0 | 0 | 0 |
| 47 | 11.2 | — | 0 | 0 | N | 0 | 0 | 0 | 0 | 0 | 0 | 0 |
| 48 | 11.2 | 0 | 0 | 1 | 1 | 0 | 0 | 0 | 0 | 0 | 0 | 1 |
| 49 | 11.2 | 0 | 0 | 0 | 0 | 0 | 0 | 0 | 0 | 0 | 0 | 0 |
| 50 | 11.2 | 0 | 0 | 0 | 0 | 0 | 0 | 0 | 0 | 0 | 0 | 0 |
| 51 | 11.2 | 0 | 0 | 1 | 1 | 0 | 0 | 0 | 0 | 0 | 0 | 1 |
| 52 | 11.2 | 0 | 1 | 1 | 1 | 1 | 0 | 0 | 0 | 0 | 0 | 1 |
| 53 | 11.2 | 0 | 0 | 1 | N | 0 | 0 | 0 | 0 | 0 | 0 | 0 |
| 54 | 11.2 | 0 | 2 | 1 | 1 | 1 | 0 | 0 | 0 | 0 | 0 | 1 |
| 55 | 11.2 | 0 | 1 | 0 | 1 | 0 | 1 | 0 | 0 | 0 | 0 | 1 |
| 56 | 11.2 | N | 0 | 0 | 0 | 0 | 0 | 0 | 0 | 0 | 0 | 1 |
| 57 | 11.2 | 0 | 1 | 1 | 1 | 0 | 0 | 0 | 0 | 0 | 0 | 0 |
| 58 | 11.2 | 0 | 0 | 0 | 0 | 0 | 0 | 0 | 0 | 0 | 0 | 0 |
| 59 | 11.2 | 0 | 0 | 1 | 1 | 0 | 0 | 0 | 0 | 0 | 0 | 0 |
| 60 | 11.2 | 0 | 0 | 0 | 0 | 0 | 0 | 0 | 0 | 0 | 0 | 0 |
| 61 | 11.2 | 0 | 0 | 0 | 0 | 0 | 0 | 0 | 0 | 0 | 0 | 1 |
| 62 | 11.2 | 0 | 0 | 0 | 0 | 0 | 0 | 0 | 0 | 0 | 0 | 0 |
| 63 | 11.2 | 0 | 0 | 0 | 0 | 0 | 0 | 0 | 0 | 0 | 0 | 0 |
| 64 | 11.2 | 0 | 0 | 0 | 0 | 0 | 0 | 0 | 0 | 0 | 0 | 0 |
| 65 | 11.2 | 0 | 0 | 0 | 1 | 0 | 0 | 0 | 0 | 0 | 0 | 0 |
| 66 | 11.2 | 0 | 0 | 1 | 0 | 0 | 0 | 0 | 0 | 0 | 0 | 0 |
| 67 | 11.2 | 0 | 0 | 0 | 0 | 0 | 0 | 0 | 0 | 0 | 0 | 0 |
| 68 | 11.2 | 0 | 0 | 0 | 0 | 0 | 0 | 0 | 0 | 0 | 0 | 0 |
| 69 | 11.2 | 0 | 0 | 0 | 0 | 0 | 0 | 0 | 0 | 0 | 0 | 0 |
| 70 | 11.2 | 0 | 0 | 0 | 0 | 0 | 0 | 0 | 0 | N | 0 | 0 |
| 71 | 11.2 | 0 | 0 | 0 | 0 | 0 | 0 | 0 | 0 | 0 | 0 | 1 |
| 72 | 11.2 | 0 | 0 | 0 | 0 | 0 | 0 | 0 | 0 | N | 0 | 0 |
| 73 | 11.2 | 0 | 0 | 0 | 0 | 1 | 0 | 0 | 0 | 0 | 0 | 0 |
| 74 | 11.2 | 0 | 0 | 0 | 0 | 0 | 0 | 0 | 0 | N | 0 | 0 |
| 75 | 11.2 | 0 | 0 | 0 | 0 | 0 | 0 | 0 | 0 | 0 | 0 | 0 |
| 76 | 11.2 | 0 | 0 | 0 | 0 | 0 | 0 | 0 | 0 | 0 | 0 | 0 |
| 77 | 11.2 | 0 | 0 | 0 | 0 | 0 | 0 | 0 | 0 | N | 0 | 0 |
| 78 | 11.2 | 0 | 0 | 0 | 0 | 0 | 0 | 0 | 0 | N | 2 | 0 |
| 79 | 11.2 | 0 | 0 | 0 | 0 | N | 0 | 0 | 0 | 0 | — | 0 |
| 80 | 11.2 | 0 | 0 | 0 | 0 | 0 | 0 | 0 | 0 | N | 0 | |

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting e.g., with kerosene, to spray concentration.

The concentration compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

HETEROCYCLIC NITROGEN/SULFUR DERIVATIVES

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil 1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

UREAS

N-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl)aminocarbonyl]-benzenesulfonamide
Methyl 2-(((((4,6-dimethyl-2-pyrimidinyl)amino)carbonyl)amino)sulfonyl)benzoate
Ethyl 2-[methyl 2-(((((4,6-dimethyl-2-pyrimidinyl)amino)carbonyl)amino)sulfonyl)]benzoate
Methyl-2((4,6-dimethoxypyrimidin-2-yl)aminocarbonyl)aminosulfonylmethyl)benzoate
Methyl 2-(((((4-methoxy-6-methyl-1,3,5-triazin-2-yl)amino)carbonyl)amino)sulfonyl)benzoate

CARBAMATES/THIOLCARBAMATES

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate

ACETAMIDES/ACETANILIDES/ANILINES/AMIDES

2-Chloro-N,N-diallylacetamide
N,N-dimethyl-2,2-diphenylacetamide
N-[2,4-dimethyl-5-[[(trifluoromethyl)sulfonyl]amino]-phenyl]acetamide N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

ACIDS/ESTERS/ALCOHOLS 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts.
Butyl 2-[4-[(5-(trifluoromethyl)-2-pyridinyl)oxy]-phenoxy]-propanoate

ETHERS 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy)ethyl 5-[2-chloro-4-(trifluoromethyl)-phenoxy]-2-nitrobenzoate

MISCELLANEOUS 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo(2.2.1)heptane, 1-methyl-4-(1-methyl ethyl)-2-(2-methylphenylmethoxy)-,exo- Fertilizers useful in combination with the active ingredients include, for example ammonium nitrate, urea, potash and superphosphate, Other useful additaments include materials in which plant organisms take root and grow such as compost, manure, humus, sand and the like.

Herbicide formulations of the types described above are exemplified in several illustrative embodiments below.

|  | Weight Percent |
|---|---|
| I. Emulsifiable Concentrates | |
| A. Compound of Example No. 3 | 11.0 |
| Free acid of complex organic phosphate or aromatic or aliphatic hydrophobe base (e.g., GAFAC RE-610, registered trademark of GAF Corp.) | 5.59 |
| Polyoxyethylene/polyoxypropylene block copolymer with butanol (e.g., Tergitol XH, registered trademark of Union Carbide Corp.) | 1.11 |
| Phenol | 5.34 |
| Monochlorobenzene | 76.96 |
| | 100.00 |
| B. Compound of Example No. 14 | 25.00 |
| Free acid of complex organic phosphate of aromatic or aliphatic hydrophobe base (e.g., GAFAC RE-610) | 5.00 |
| Polyoxyethylene/polyoxypropylene block copolymer with butanol (e.g., Tergitol XH) | 1.60 |
| Phenol | 4.75 |
| Monochlorobenzene | 63.65 |
| | 100.00 |
| II. Flowables | |
| A. Compound of Example No. 24 | 25.00 |
| Methyl cellulose | 0.3 |
| Silica Aerogel | 1.5 |
| Sodium lignosulfonate | 3.5 |
| Sodium N—methyl-N—oleyl taurate | 2.0 |
| Water | 67.7 |
| | 100.00 |
| B. Compound of Example No. 18 | 45.0 |
| Methyl cellulose | .3 |
| Silica aerogel | 1.5 |
| Sodium lignosulfonate | 3.5 |
| Sodium N—methyl-N—oleyl taurate | 2.0 |
| Water | 47.7 |
| | 100.00 |
| III. Wettable Powders | |
| A. Compound of Example No. 5 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example 21 | 80.00 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 6 | 10.0 |
| Sodium lignosulfonate | 3.0 |
| Sodium N—methyl-N—oleyl-taurate | 1.0 |
| Kaolinite clay | 86.0 |
| | 100.00 |
| IV. Dusts | |
| A. Compound of Example No. 13 | 2.0 |
| Attapulgite | 98.0 |
| | 100.00 |
| B. Compound of Example No. 10 | 60.0 |
| Montmorillonite | 40.0 |
| | 100.00 |
| C. Compound of Example No. 54 | 30.0 |
| Ethylene glycol | 1.0 |
| Bentonite | 69.0 |
| | 100.00 |
| D. Compound of Example No. 62 | 1.0 |
| Diatomaceous earth | 99.0 |

-continued

|  | Weight Percent |
|---|---|
| | 100.00 |
| V. Granules | |
| A. Compound of Example No. 52 | 15.0 |
| Granular attapulgite (20/40 mesh) | 85.0 |
| | 100.00 |
| B. Compound of Example No. 70 | 30.0 |
| Diatomaceous earth (20/40) | 70.0 |
| | 100.00 |
| C. Compound of Example No. 58 | 1.0 |
| Ethylene glycol | 5.0 |
| Methylene blue | 0.1 |
| Pyrophyllite | 93.9 |
| | 100.00 |
| D. Compound of Example No. 46 | 5.0 |
| Pyrophyllite (20/40) | 95.0 |
| | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1981). Thus, the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations.

We claim:

1. A compound represented by the generic formula

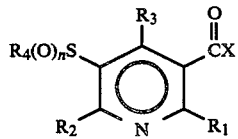

wherein:

n is from 0 to 2 inclusive; X is selected from the group consisting of a halogen, hydroxy, lower alkoxy, lower alkenoxy, lower alkynoxy, haloalkoxy, haloalkenoxy, and alkylthio;

$R_1$ and $R_2$ are independently selected from fluorinated methyl and chlorofluorinated methyl radicals, provided that one of $R_1$ and $R_2$ must be fluorinated methyl;

$R_4$ is selected from lower alkyl, hydrogen, $C_{4-6}$ cycloalkyl, phenyl, benzyl, cyano, amino, and lower alkylamino;

$R_3$ is selected from hydroxy, lower alkoxy, loweralkylthio, lower alkylsulfonyl, lower alkyl, $C_{4-6}$ cycloalkyl, $C_{4-6}$ cycloalkyl lower alkyl;

provided that when n is 0 or 2, $R_4$ is not phenyl, and further provided that when $R_3$ is methyl and $R_4$ is methyl, ethyl, or t-butyl, n is not 1 or 2.

2. A compound according to claim 1 wherein one of $R_1$ and $R_2$ is trifluoromethyl and the other is difluoromethyl.

3. A compound according to claim 2 wherein X is selected from alkoxy and alkylthio.

4. A compound according to claim 3 wherein $R_4$ is lower alkyl.

5. A compound according to claim 4 wherein $R_3$ is selected from cyclobutyl, 2-methylpropyl, and n-propyl.

6. A compound according to claim 5 wherein n is zero.

7. A compound according to claim 5 wherein n is one.

8. A compound according to claim 5 wherein n is two.

9. A herbicidal composition comprising an adjuvant and an active ingredient represented by the generic formula

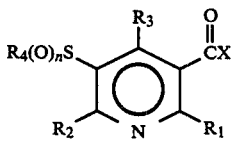

wherein:

n is from 0 to 2 inclusive; X is selected from the group consisting of a halogen, hydroxy, lower alkoxy, lower alkenoxy, lower alkynoxy, haloalkoxy, haloalkenoxy, and alkylthio;

$R_1$ and $R_2$ are independently selected from fluorinated methyl and chlorofluorinated methyl radicals, provided that one of $R_1$ and $R_2$ must be fluorinated methyl;

$R_4$ is selected from lower alkyl, hydrogen, $C_{4-6}$ cycloalkyl, phenyl, benzyl, cyano, amino, and lower alkylamino;

$R_3$ is selected from hydroxy, lower alkoxy, loweralkylthio, lower alkylsulfonyl, lower alkyl, $C_{4-6}$ cycloalkyl, $C_{4-6}$ cycloalkyl lower alkyl;

provided that when n is 0 or 2, $R_4$ is not phenyl, and further provided that when $R_3$ is methyl and $R_4$ is methyl, ethyl, or t-butyl, n is not 1 or 2.

10. A composition according to claim 9 wherein one of $R_1$ and $R_2$ is trifluoromethyl and the other is difluoromethyl.

11. A composition according to claim 10 wherein X is selected from alkoxy and alkylthio.

12. A composition according to claim 11 wherein $R_4$ is lower alkyl.

13. A composition according to claim 12 wherein $R_3$ is selected from cyclobutyl, 2-methylpropyl, and n-propyl.

14. A composition according to claim 13 wherein n is zero.

15. A composition according to claim 13 wherein n is one.

16. A composition according to claim 13 wherein n is two.

17. A method of controlling undesired vegetation comprising applying to the plant locus an effective amount of a compound represented by the generic formula

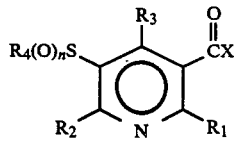

wherein:

n is from 0 to 2 inclusive; X is selected from the group consisting of a halogen, hydroxy, lower alkoxy, lower alkenoxy, lower alkynoxy, haloalkoxy, haloalkenoxy, and alkylthio;

$R_1$ and $R_2$ are independently selected from fluorinated methyl and chlorofluorinated methyl radicals, provided that one of $R_1$ and $R_2$ must be fluorinated methyl;

$R_4$ is selected from lower alkyl, hydrogen, $C_{4-6}$ cycloalkyl, phenyl, benzyl, cyano, amino, and lower alkylamino;

$R_3$ is selected from hydroxy, lower alkoxy, loweralkylthio, lower alkylsulfonyl, lower alkyl, $C_{4-6}$ cycloalkyl, $C_{4-6}$ cycloalkyl lower alkyl;

provided that when n is 0 or 2, $R_4$ is not phenyl and further provided that when $R_3$ is methyl and $R_4$ is methyl, ethyl, or t-butyl, n is not 1 or 2.

18. A method according to claim 17 wherein one of $R_1$ and $R_2$ is trifluoromethyl and the other is difluoromethyl.

19. A method according to claim 18 wherein X is selected from alkoxy and alkylthio.

20. A method according to claim 19 wherein $R_4$ is lower alkyl.

21. A method according to claim 20 wherein $R_3$ is selected from cyclobutyl, 2-methylpropyl, and n-propyl.

22. A method according to claim 21 wherein n is zero.

23. A method according to claim 21 wherein n is one.

24. A method according to claim 21 wherein n is two.

* * * * *